US008957960B2

(12) United States Patent
Saylor et al.

(10) Patent No.: US 8,957,960 B2
(45) Date of Patent: Feb. 17, 2015

(54) MACHINE VISION SYSTEM PROGRAM EDITING ENVIRONMENT INCLUDING REAL TIME CONTEXT GENERATION FEATURES

(75) Inventors: Barry Saylor, Kent, WA (US); Dahai Yu, Redmond, WA (US); Ryan Northrup, Renton, WA (US); Gyokubu Cho, Kawasaki (JP); Akira Takada, Yokohama (JP)

(73) Assignee: Mitutoyo Corporation, Kawasaki-shi (JP)

( * ) Notice: Subject to any disclaimer, the term of this patent is extended or adjusted under 35 U.S.C. 154(b) by 760 days.

(21) Appl. No.: 13/297,232

(22) Filed: Nov. 15, 2011

(65) Prior Publication Data

US 2013/0123945 A1    May 16, 2013

(51) Int. Cl.
*G06F 3/00* (2006.01)
*G06F 9/44* (2006.01)
*G06F 9/45* (2006.01)
*G05B 13/02* (2006.01)
*G05B 19/18* (2006.01)
*G05B 15/00* (2006.01)
*G05B 19/42* (2006.01)
(Continued)

(52) U.S. Cl.
CPC ................ *G06F 8/30* (2013.01); *G05B 19/409* (2013.01); *G05B 19/4093* (2013.01); *G01N 21/8851* (2013.01); *G05B 2219/35505* (2013.01); *G05B 2219/36143* (2013.01);
(Continued)

(58) Field of Classification Search
None
See application file for complete search history.

(56) References Cited

U.S. PATENT DOCUMENTS 4,835,730 A    5/1989  Shimano
5,481,712 A    1/1996  Silver
(Continued)

OTHER PUBLICATIONS

"QVPAK 3D CNC Vision Measuring Machine: Operation Guide," Version 2.0, Manual No. 4911GB, Series No. 359, Mitutoyo Corporation & Micro Encoder Inc., Kanagawa, Japan, Sep. 1996, 86 pages.
(Continued)

*Primary Examiner* — Joseph Ustaris
*Assistant Examiner* — William Adrovel
(74) *Attorney, Agent, or Firm* — Christensen O'Connor Johnson Kindness PLLC

(57) ABSTRACT

A machine vision system program editing environment includes near real time context generation. Rather than requiring execution of all preceding instructions of a part program in order to generate a realistic context for subsequent edits, surrogate data operations using previously saved data replace execution of certain sets of instructions. The surrogate data may be saved during the actual execution of operations that are recorded in a part program. An edit mode of execution substitutes that data as a surrogate for executing the operations that would otherwise generate that data. Significant time savings may be achieved for context generation, such that editing occurs within an operating context which may be repeatedly refreshed for accuracy in near real time. This supports convenient program modification by relatively unskilled users, using the native user interface of the machine vision system, rather than difficult to use text-based or graphical object-based editing environments.

41 Claims, 18 Drawing Sheets

(51) Int. Cl.
*G06F 19/00* (2011.01)
*G06F 17/00* (2006.01)
*G05B 19/409* (2006.01)
*G05B 19/4093* (2006.01)
*G01N 21/88* (2006.01)

(52) U.S. Cl.
CPC ............... *G05B 2219/36172* (2013.01); *G05B 2219/37208* (2013.01); *G05B 2219/37439* (2013.01); *G05B 2219/37455* (2013.01); *Y10S 715/964* (2013.01); *Y10S 715/965* (2013.01); *Y10S 715/97* (2013.01)
USPC ............ 348/86; 715/700; 715/707; 715/771; 715/964; 715/965; 715/970; 717/104; 717/105; 717/106; 717/109; 717/110; 717/112; 717/113; 717/114; 717/127; 717/130; 717/131; 717/143; 717/155; 717/156; 717/158; 700/28; 700/29; 700/30; 700/31; 700/59; 700/60; 700/61; 700/64; 700/83; 700/86; 700/87; 700/88; 700/98; 700/114; 700/143; 700/204; 700/244; 700/17; 348/92; 348/135

(56) References Cited

U.S. PATENT DOCUMENTS

| | | |
|---|---|---|
| 5,537,546 A | 7/1996 | Sauter |
| 6,016,467 A | 1/2000 | Newsted |
| 6,542,180 B1 | 4/2003 | Wasserman |
| 6,636,211 B2 | 10/2003 | Chartier |
| 7,055,092 B2 | 5/2006 | Yardumian |
| 7,207,017 B1 | 4/2007 | Tabery |
| 7,324,682 B2 | 1/2008 | Wasserman |
| 7,376,904 B2 | 5/2008 | Cifra |
| 7,454,053 B2 | 11/2008 | Bryll |
| 7,590,276 B2 | 9/2009 | Delaney |
| 7,643,907 B2 | 1/2010 | Fuhlbrigge |
| 7,689,634 B2 | 3/2010 | Agarwal |
| 7,864,178 B2 | 1/2011 | Marini |
| 8,028,085 B2 | 9/2011 | Elien |
| 8,111,905 B2 | 2/2012 | Campbell |
| 8,111,938 B2 | 2/2012 | Bryll |
| 2006/0150148 A1 | 7/2006 | Beckett |
| 2006/0178778 A1 | 8/2006 | Fuhlbrigge |
| 2007/0067290 A1 | 3/2007 | Makela |
| 2007/0150102 A1 | 6/2007 | Park |
| 2007/0250204 A1 | 10/2007 | Ould |
| 2009/0164202 A1 | 6/2009 | Lönnemark |
| 2010/0103679 A1 | 4/2010 | Lee |
| 2010/0158343 A1 | 6/2010 | Bryll |
| 2010/0269094 A1 | 10/2010 | Levenshteyn |
| 2011/0103679 A1 | 5/2011 | Campbell |
| 2013/0120553 A1 | 5/2013 | Delaney |
| 2013/0120567 A1 | 5/2013 | Northrup |

OTHER PUBLICATIONS

"QVPAK 3D CNC Vision Measuring Machine: User's Guide," Version 7.1, 2d ed., Manual No. 99MCB225A, Series No. 359, Mitutoyo Corporation & Micro Encoder Inc., Kanagawa, Japan, Sep. 2003, 370 pages.

```
<Measure breakpoint="FALSE" nodeID="{B4969AD8-FE38-4F4D-A9C9-9A455082CBDA}" returnCode="MIML_OK" blockMarker="FALSE" simulationStatus="good">
    <ImageSetContext breakpoint="FALSE" nodeID="{C6C9D82A-F67A-4D07-8394-72236F4AB5AE}" returnCode="MIML_OK" blockMarker="FALSE" simulationStatus="good">
        <x>1.998521000</x>
        <y>1.998199531</y>
        <z>-0.002600000</z>
        <coax>0</coax>
    </ImageSetContext>
    <BoxTool breakpoint="FALSE" nodeID="{0197EFDA-BE83-45B3-AFAF-B0C47E4D2BC5}" returnCode="MIML_OK" blockMarker="FALSE" simulationStatus="good">
        <vcs>FALSE</vcs>
        <x>2.310056547</x>
        <y>2.000848736</y>
        <z>-0.002700000</z>
        <w>0.196000000</w>
        <h>0.574280000</h>
    <standardDetection>
        <step1>
            <addDetectN1>0</addDetectN1>
            <addDetectD1>0.000000000</addDetectD1>
            <addDetectD2>0.000000000</addDetectD2>
            <addDetectD3>0.000000000</addDetectD3>
            <addDetectD4>0.000000000</addDetectD4>
        </step1>
    </standardDetection>
```

```xml
<filterType>@</filterType>
    <dllName>@</dllName>
    <paramList>@</paramList>
    <scanInterval>20</scanInterval>
    <samplingDirection>LEFT</samplingDirection>
    <simulationData>
        <SimDataPoints>
            <SimDataPoint type="xyz" x="2.5845592666892459" y="1.9996700697272724" z="-0.0026000000000001046"/>
            <SimDataPoint type="xyz" x="2.5453593842225082" y="1.9995709619830341" z="-0.0026000000000001046"/>
            <SimDataPoint type="xyz" x="2.5061586571484666" y="1.9999183284286433" z="-0.0026000000000001046"/>
            <SimDataPoint type="xyz" x="2.4669588355505851" y="1.9997869543609266" z="-0.0026000000000001046"/>
        </SimDataPoints>
    </simulationData>
</BoxTool>
<DefineLine breakpoint="FALSE" nodeID="{C9A83BEB-3A17-4D9B-8DEB-C964FC5F1D82}" returnCode="MIML_OK" blockMarker="FALSE" simulationStatus="good">
    <featureLabel>L3</featureLabel>
    <x>2.310158654</x>
    <y>1.9997348854</y>
    <z>-0.002600000</z>
</DefineLine>
</Measure>
```

530 (brace around SimDataPoint lines)
561C (pointing to DefineLine)

```xml
<Measure breakpoint="FALSE" nodeID="{B4969AD8-FE38-4F4D-A9C9-9A455082CBDA}" returnCode="MIML_OK" blockMarker="FALSE" simulationStatus="good">
    <ImageSetContext breakpoint="FALSE" nodeID="{C6C9D82A-F67A-4D07-8394-72236F4AB5AE}" returnCode="MIML_OK" blockMarker="FALSE" simulationStatus="good">
        <x>1.998521000</x>
        <y>1.998199531</y>
        <z>-0.002600000</z>
        <coax>0</coax>
    </ImageSetContext>
    <BoxTool breakpoint="FALSE" nodeID="{0197EFDA-BE83-45B3-AFAF-B0C47E4D2BC5}" returnCode="MIML_OK" blockMarker="FALSE" simulationStatus="good">
        <vcs>FALSE</vcs>
        <x>2.435119311</x>
        <y>1.999505290</y>
        <z>-0.010100000</z>
        <w>0.196000000</w>
        <h>0.325360000</h>
    </BoxTool>
    <standardDetection>
        <step1>
            <addDetectN1>0</addDetectN1>
            <addDetectD1>0.000000000</addDetectD1>
            <addDetectD2>0.000000000</addDetectD2>
            <addDetectD3>0.000000000</addDetectD3>
            <addDetectD4>0.000000000</addDetectD4>
        </step1>
    </standardDetection>
```

```
<filterType>@</filterType>
    <dllName>@</dllName>
    <paramList>@</paramList>
    <scanInterval>20</scanInterval>
    <samplingDirection>LEFT</samplingDirection>
    <simulationData>
        <SimDataPoints>
            <SimDataPoint type="xyz" x="2.5919178738878963" y="2.0004135736673883" z="-0.0101000000000000133"/>
            <SimDataPoint type="xyz" x="2.5527175731873165" y="2.0005354927776475" z="-0.0101000000000000133"/>
            <SimDataPoint type="xyz" x="2.5135165460338990" y="2.0010415222203465" z="-0.0101000000000000133"/>
        </SimDataPoints>
    </simulationData>
</BoxTool>
<DefineLine breakpoint="FALSE" nodeID="{C9A83BEB-3A17-4D9B-8DEB-C964FC5F1D82}" returnCode="MIML_OK" blockMarker="FALSE" simulationStatus="good">
    <featureLabel>L3</featureLabel>
    <x>2.310158654</x>
    <y>1.999734885</y>
    <z>-0.002600000</z>
</DefineLine>
</Measure>
```

1130 (brace around three SimDataPoint lines)

MACHINE VISION SYSTEM PROGRAM EDITING ENVIRONMENT INCLUDING REAL TIME CONTEXT GENERATION FEATURES

FIELD OF THE INVENTION

The invention relates generally to machine vision inspection systems, and more particularly to methods for creating and editing part programs in such systems.

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode." Once the inspection event sequence is defined in "learn mode," such a sequence can then be used to automatically acquire (and additionally analyze or inspect) images of a workpiece during "run mode."

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs." Video tools may include, for example, edge/boundary detection tools, autofocus tools, shape or pattern matching tools, dimension measuring tools, and the like. Other graphical user interface features may include dialog boxes related to data analysis, step and repeat loop programming, and the like. For example, such tools are routinely used in a variety of commercially available machine vision inspection systems, such as the QUICK VISION® series of vision systems and the associated QVPAK® software, discussed above.

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Editing a part program for a machine vision inspection system is a more complex task than editing a program for a machine tool or assembly robot or the like. For example, part programs for machine vision inspection systems include later portions that control operations and/or provide image-dependent measurement results that depend at least partially on the results determined by the execution of a previous portion of the program and/or on the particular instance of a workpiece that is being used to provide the images that are essential to the inspection operations. Furthermore, the required lighting and/or exposure time required for a particular image may depend on a particular instance of a workpiece. Furthermore, if a user saves a partially completed part program and recalls the part program at a later time to alter or finish the programming, it may be unknown if certain types of changes have occurred in the interim (e.g., changes in environmental conditions, the part being inadvertently moved on the stage, etc.) that may adversely affect the continuing edits to the part program. Due to such concerns, it has been a standard practice for some such systems to actually execute all of the instructions of a part program from the beginning, up to, and including any potential additional modifications or additions to the part program instructions, in order to verify that the modifications and/or additions are being programmed based on a realistic set of conditions for their operation. However, the execution of all of the instructions of a part program to provide a realistic operating condition for modifications or additions to the instructions is impractical for a large part program (e.g., those including a large number of image acquisitions, and/or feature inspections), which is particularly common for machine vision inspection systems that provide microscopic inspection (e.g., micron resolution measurements) on macroscopic objects (e.g., objects spanning tens or hundreds of millimeters). A need exists for an editing environment that can reliably update operating conditions in a short time (e.g., nearly "real time") during editing operations and to allow more rapid, efficient, intuitive, and flexible and robust creation and editing of part programs for precision machine vision inspection systems.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

According to the considerations outlined above, it would be desirable for a machine vision inspection system to provide near real time updates to the operating context when editing a part program, in order to verify that, at the time modifications and/or additions are programmed, a realistic set of operating conditions are available as the basis or context for the modifications and/or additions. This is particularly important when the part program is created and edited by recording actual control operations input by a user of the machine vision inspection system, in that the user is intuitively selecting the details of their input operations based on the state of the machine vision inspection system and/or the appearance and location of the images that are present at the time that they are providing their input operations, and so on. Thus, the user cannot begin a valid and reliable modification of a part program at an arbitrary location in the part program, without first establishing the system in substantially the same operating context at that location as would be provided by the execution of the previous instructions of the part program during their automatic mode of execution during run mode. Heretofore, no general purpose machine vision inspection system, and particularly no system which records actual user controlled operations in order to create a part program (e.g., as opposed to simple graphical object or text-based programming systems), have provided an editing environment which reliably and robustly provides a valid part programming editing context in near real time, during editing operations.

In order to support this desirable editing environment, a machine vision system program editing environment including real time context generation features is disclosed herein. The machine vision inspection system includes an imaging portion, a stage for holding one or more workpieces in a field of view (FOV) of the imaging portion, a control portion, a display, and a user interface.

In various embodiments, the machine vision inspection system further comprises a run mode, a learn mode, and an editing portion. The run mode is operable to execute a previously-created part program using a run mode of execution. The learn mode is operable to receive user input to control operations of the machine vision inspection system and record part program instructions corresponding to the controlled operations in order to create a part program. The learn mode also includes an editing user interface comprising an editable part program representation of part program instructions, wherein the part program representation comprises instruction representations. The editing portion is operable to edit a part program and includes an editing execution portion operable to execute previously recorded part program instructions according to an edit mode of execution that is different than the run mode of execution.

In various embodiments, the learn mode is configured such that it is further operable to automatically record respective surrogate data which is associated with a respective set of recorded part program instructions, wherein at least some of the surrogate data includes data which results from actual control operations corresponding to the associated set of recorded instructions. In addition, the edit mode of execution includes a surrogate execution mode. During the surrogate execution mode, for at least one set of part program instructions, if respective surrogate data has been previously recorded in association with that set of part program instructions, then at least some members of that set of part program instructions are not executed. In other words, the corresponding associated actual control operations are not executed, and the respective surrogate data is used in the subsequent operation of the surrogate execution mode as a substitute for data that would otherwise result from those actual control operations which are not executed.

In various embodiments, creating a part program may comprise modifying a previously recorded part program instruction.

In various embodiments, respective surrogate data may comprise data which results from actual execution of controlled operations that are controlled based on received user input, and those controlled operations are recorded to provide the associated respective set of recorded part program instructions.

In various embodiments, the edit mode of execution comprises an actual execution mode, and at least some respective surrogate data comprises data which results from actual execution of controlled operations that are controlled based on executing a previously recorded associated respective set of recorded part program instructions using the actual execution mode.

In various embodiments, the machine vision inspection system may comprise a program status managing portion that is operable to save the recorded part program instructions in an editable part program file, and when the recorded part program instructions are saved as an editable part program file, respective surrogate data which is associated with a respective set of recorded part program instructions in the editable part program file are also saved. In some embodiments, the machine vision inspection system is operable to load the saved editable part program file for editing, and the machine vision inspection system is configured such that when the saved editable part program file is loaded for editing, the associated saved respective surrogate data are automatically made available for use in the surrogate execution mode. In one implementation, the program status managing portion is further operable to save the recorded part program instructions in a protected part program file that is executable using the run mode of execution, wherein at least one of the run mode of execution and the protected part program file is configured such that the results of the run mode of execution are not affected by any previously recorded surrogate data corresponding to the protected part program file. In some embodiments, the learn mode is configured to record in a respective set of recorded part program instructions an indication of whether respective surrogate data has been previously recorded in association with that respective set of part program instructions, and the program status managing portion is configured to remove indications of whether respective surrogate data has been previously recorded in association with a respective set of part program instructions, prior to saving the recorded part program instructions in the protected part program file.

In various embodiments, the learn mode may be configured to record in a respective set of recorded part program instructions an indication of whether respective surrogate data has been previously recorded in association with that respective set of part program instructions. In one embodiment, the indication is included in an initial instruction of the respective set of recorded part program instructions. In one embodiment, the respective set of recorded part program instructions may comprise instructions written in a mark-up language (e.g., XML, or a derivative thereof). In various embodiments, the respective set of recorded part program instructions may comprise at least one of an element, a parent element, a container element, and a child element written in the mark-up language. In one embodiment, the indication may comprise the presence of respective surrogate data included within that respective set of recorded part program instructions. In one embodiment, the indication may comprise a respective identifier included within that respective set of recorded part program instructions, the respective identifier usable to locate the corresponding respective surrogate data in a surrogate data memory portion of the machine vision inspection system.

In various embodiments, the editing portion comprises editing commands usable to edit a part program, and the editing execution portion is configured such that when the user uses the editing user interface to input an editing command to edit the program at a target location indicated in the part program representation, then the edit mode of execution begins at a valid context starting location in the part program prior to the target location, and uses the surrogate execution mode for executing at least a portion of the part program instructions, in order to establish a valid context for editing the part program at the target location.

In various embodiments an input editing command may be a command for modifying a part program at the target location, and the part program instruction located at the target location may be a previously recorded part program instruction that is to be modified. In one embodiment, the input editing command may be a command for inserting or appending instructions into the part program at the target location, and the part program instruction located at the target location may be a part program instruction that is to be created and inserted or appended at the target location. In one embodiment, establishing the valid context at the target location includes establishing the hardware state of the machine vision inspection system in an expected or proper state for executing control operations corresponding to a part program instruction located at the target location. In one embodiment, the valid context starting location in the part program comprises one of (a) the beginning of the part program instructions and (b) the next instruction after a previously executed editing initialization block comprising part program instructions. Such an editing initialization block is disclosed in "System and Method Utilizing An Editing Initialization Block In A Part Program Editing Environment In A Machine Vision System" (Ser. No. 13/297,182) which is filed concurrently herewith, and hereby incorporated herein by reference. In order to further clarify the meaning of a "valid context" starting location in a part program, by way of example and not by way of limitation, it means that execution of the part program can begin at that particular location with the machine vision inspection in an expected or proper state for executing the next control operation and/or corresponding part program instruction at or following that particular location. By way of example and not by way of limitation, another type of valid context starting location may in some instances be immediately preceding an executable set of part program instructions which include a complete set of previously stored system software and hardware state parameters or variables corresponding to that location in the part program instructions, wherein that set of part program instructions can then be executed to establish or reestablish an operationally equivalent software and hardware state at that location of the part program instructions. Another type of valid context starting location may in some instances be immediately after the stopping location of actually executing the part program instructions after beginning from a valid context starting location. Another type of valid context starting location may in some instances be immediately after the stopping location of executing the part program instructions in surrogate execution mode, as disclosed herein, after beginning from a valid context starting location.

In one embodiment, the learn mode is configured such that when the edit execution mode establishes a valid context at a target location, the learn mode user interface is configured to display learn mode user interface elements that are operable by a user to edit and insert part program instructions at the target location, and those learn mode user interface elements comprise video tool selection elements. In one embodiment, the learn mode is configured such that when the valid context is established at the target location, the learn mode user interface is configured to display a context status indicator proximate to the indication of the target location indicated in the part program representation, and the context status indicator is set to indicate that a valid context has been established at the target location. In one embodiment, the learn mode is configured such that when the edit mode of execution uses the surrogate execution mode for executing at least a portion of the part program instructions in order to establish the valid context, then the state of the context status indicator is set to a state that specifically indicates that surrogate execution mode has been used to establish the valid context. In one embodiment, the context status indicator is an instruction pointer included proximate to the editable part program representation. In one embodiment, the edit mode of execution comprises an actual execution mode which provides actual execution of controlled operations that are controlled based on executing a previously recorded set of part program instructions, and the editing user interface includes a control operable by the user to use the actual execution mode for executing a set of part program instructions that are sufficient to establish a valid context for editing the part program at a target location. In one embodiment, the learn mode is configured such that when the edit mode of execution uses exclusively the actual execution mode for executing the part program instructions that are sufficient to establish the valid context, then the context status indicator is set to a state that specifically indicates that actual execution mode has been used to establish the valid context. In one embodiment, the learn mode is configured such that when a valid context has not been established at the target location, then the state of the context status indicator is set to indicate that the context is at least one of unknown or not valid. In one embodiment, the edit mode of execution by default automatically begins at the valid context starting location. In one embodiment, the edit mode of execution by default automatically uses the surrogate execution mode for executing at least a portion of the part program instructions. In one embodiment, the edit mode of execution comprises an actual execution mode which provides actual execution of controlled operations that are controlled based on executing a previously recorded set of part program instructions, and when the target location is represented within a target parent element represented in the editable part program representation, then surrogate execution mode comprises switching to the actual execution mode at a starting location of part program instructions corresponding to the target parent element. In one embodiment, the target location comprises an instruction that controls an operation corresponding to a video tool that analyzes an acquired image, and the target parent element comprises an instruction that controls an operation of the machine vision inspection system in order to set up the image acquisition conditions for the acquired image. In one embodiment, the edit mode of execution comprises an actual execution mode which provides actual execution of controlled operations that are controlled based on executing a previously recorded set of part program instructions, and surrogate execution mode comprises switching to actual execution mode of part program instructions for instructions that unconditionally require physical system changes in order to establish the valid context. In one embodiment, the edit mode of execution comprises an actual execution mode which provides actual execution of controlled operations that are controlled based on executing a previously recorded set of part program instructions, and surrogate execution mode comprises switching to actual execution mode for a set of part program instructions which provide results data during run mode execution and for which the corresponding surrogate data is not currently recorded for use as a substitute for the results data that would otherwise result from their associated controlled operations. In one embodiment, the edit mode of execution comprises an actual execution mode which provides actual execution of controlled operations that are controlled based on executing a previously recorded set of part program instructions, and surrogate execution mode comprises switching to actual execution mode for at least some part program instructions that control operations that change the physical location of the stage relative to the imaging portion, and the learn mode user interface comprises a query box that asks if the user approves of actual execution mode operations comprising moving the physical location stage prior to the actual execution of that move.

In various embodiments, the edit mode of execution is configured such that, when at least one of the previously recorded part program instructions is modified to provide a modified part program instruction using editing commands, and the modified part program instruction is accepted for recording in the part program, the associated control operations are actually executed and the associated surrogate data is generated and saved. In one embodiment, the surrogate data is derived from analysis of workpiece images of an actual workpiece positioned on the stage, wherein the images are acquired during a period corresponding to the modification and recording of the modified part program instruction.

In various embodiments, the set of part program instructions includes instructions that perform image acquisition operations and an edge detection video tool comprising edge detection operations that identify the edge point positions of points located along a detected edge in that acquired image, if executed, and the surrogate data comprises edge point positions. In one embodiment, during the surrogate execution mode, at least the image acquisition operations and the edge detection operations are not executed.

In various embodiments, the machine vision inspection system is a software emulator of an actual machine vision inspection system that emulates the controlled hardware of that actual machine vision inspection system such that it supports virtual operation by part program instructions usable on the actual machine vision inspection system, and by controlled operations input by the user through the user interface of the machine vision inspection system. In one embodiment, the workpiece comprises a workpiece data configured to provide a virtual workpiece that operates in conjunction with the software emulator of the actual machine vision inspection system.

In some embodiments, the learn mode comprises a learn mode user interface including a results window that displays results due to the execution of part program instructions, and learn mode is configured such that when the particular results are surrogate data results based on using the surrogate execution mode for execution of part program instructions, then the learn mode user interface is configured to display a results status indicator proximate to the surrogate data results, and the results status indicator is set to indicate that those particular results are based on surrogate data. In one embodiment, the results window may appear approximately as disclosed in a patent applications entitled "Machine Vision System Program Editing Environment Including Synchronized User Interface Features" (61/560,278); which is filed concurrently herewith and hereby incorporated by reference. In various embodiments, each time a result is based on surrogate data and is displayed in the results window, the results status indicator comprises representing that surrogate data-based result with a particular color of text, or a particular color of highlighting on that text, or the like.

With regard to context, in order to further clarify the meaning of a "context" or operating context in relation to an editing environment, by way of explanation and not by way of limitation, when continuing edits are being made to a part program in a user interface, it is desirable to know and implement particular parameters at particular editing locations in the part program. For example, in order to set the correct thresholds, size and location for a video tool, it is necessary to have the expected video image including information such as the correct stage position, light levels, magnification, etc. In one embodiment, the "hardware context" may be defined as comprising this type of information. In addition, in order to know if a sequence is correct for continuing edits to the part program, it is useful to know what has been done already, including what features have been measured, what part of the coordinate system is being utilized, etc. In one embodiment, the "software context" may be defined as comprising this type of information. It will be appreciated that, according to various features outlined above and disclosed herein, accurate context may be provided as a part program is initially recorded, and also, later, during the run mode, in a circumstance where all of the instructions have been executed in order. This provides a valid context for continuing edits to the part program, including indicating any measurements and results already produced by the part program.

It should be appreciated that providing a simple, time-efficient and robust editing environment for machine vision part programs is significantly more difficult than providing an adequate editing environment for editing simple computer programs, because potentially dangerous motions and mechanical collisions must be revealed and considered during the program editing process. In addition, providing a simple, time-efficient and robust editing environment for editing machine vision part programs is significantly more difficult than providing an adequate editing environment for editing assembly robot programs and the like (e.g., programs which control a robot's geometric motions and actuators, and the like), because unique workpiece geometries and surface finishes require that unpredictable and subtle lighting and imaging effects be revealed and considered and customized during the program editing process. In addition, machine vision inspection systems are required to perform operations that determine relationships between features that are measured and inspected at different locations on a workpiece and at different points in time, by respective operations that may be dispersed throughout a part program. Thus, providing a robust editing environment that allows a relatively unskilled user to edit an existing part program beginning at an arbitrary point within the program is a difficult task. It should be appreciated based on the disclosure herein that the surrogate execution mode and methods disclosed herein are of particular utility in contributing to a solution to the combination of problems outlined above (e.g., the need to provide for rapid execution to establish context for editing, etc.), which are unique to providing a time-efficient and robust editing environment for part programs for a general purpose machine vision inspection system.

The methods of the present invention are advantageous, in that when editing a part program, rather than requiring execution of all preceding instructions of a part program in order to generate a realistic context for subsequent edits, surrogate data operations using previously saved data replace execution of certain sets of instructions. The surrogate data may be saved during the actual execution of operations that are recorded in a part program. The edit mode of execution disclosed herein substitutes that data as a surrogate for executing the operations that would otherwise generate that data through time-consuming operations. Significant time savings may be achieved for context generation, such that editing may occur within an operating context which may be repeatedly refreshed for accuracy in near real time. This supports convenient program modification by relatively unskilled users, using the native user interface of the machine vision system, rather than using a difficult-to-use text-based or graphical object-based editing environment without experiencing a reliably realistic operating context.

It should be noted that the surrogate execution mode disclosed herein differs from previously known simulation methods used for creating and editing various types of programs, in that execution of various operations is not merely simulated (e.g., using a simulated workpiece, or the like), but is actually suppressed—using the surrogate data in place of actual execution. Furthermore, the surrogate data may be exceptionally realistic, since it may be result from actual inspection operations on an actual workpiece in various embodiments. This is particularly advantageous, and even necessary, for some machine vision inspection systems. The methods disclosed herein may provide a particularly fast and particularly realistic and accurate editing environment, which is uniquely required and uniquely suited to machine vision inspection systems.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 5A and 5B are diagrams of mark-up language code instructions of the part program which correspond to some of the instruction representations of FIG. 3;

FIGS. 11A and 11B are diagrams of mark-up language code instructions which include surrogate data that has been altered according to the modification that is illustrated in FIGS. 10A and 10B;

DETAILED DESCRIPTION

Figure 1:
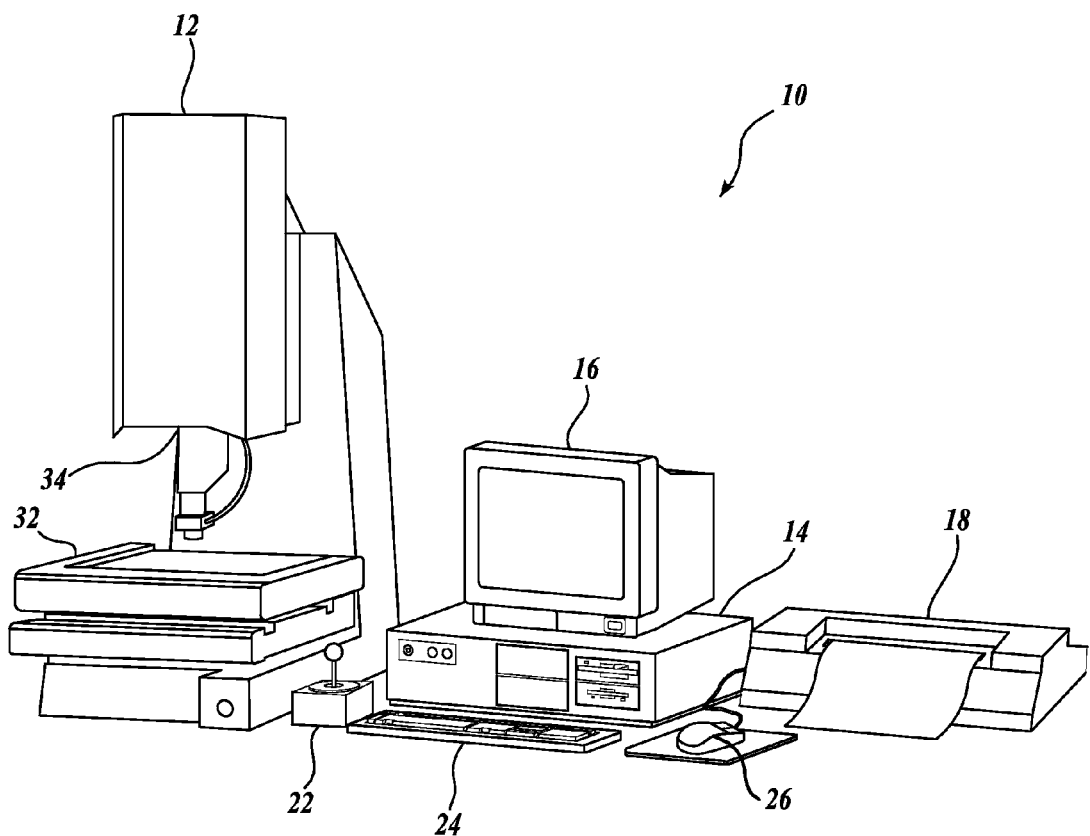
FIG. 1 is a diagram showing various typical components of a general purpose precision machine vision inspection system.

FIG. 1 is a block diagram of one exemplary machine vision inspection system 10 usable in accordance with the methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053 and 7,324,682, and U.S. Patent Publication Nos. 2010/0158343 and 2011/0103679, which are each incorporated herein by reference in their entireties.

Figure 2A:
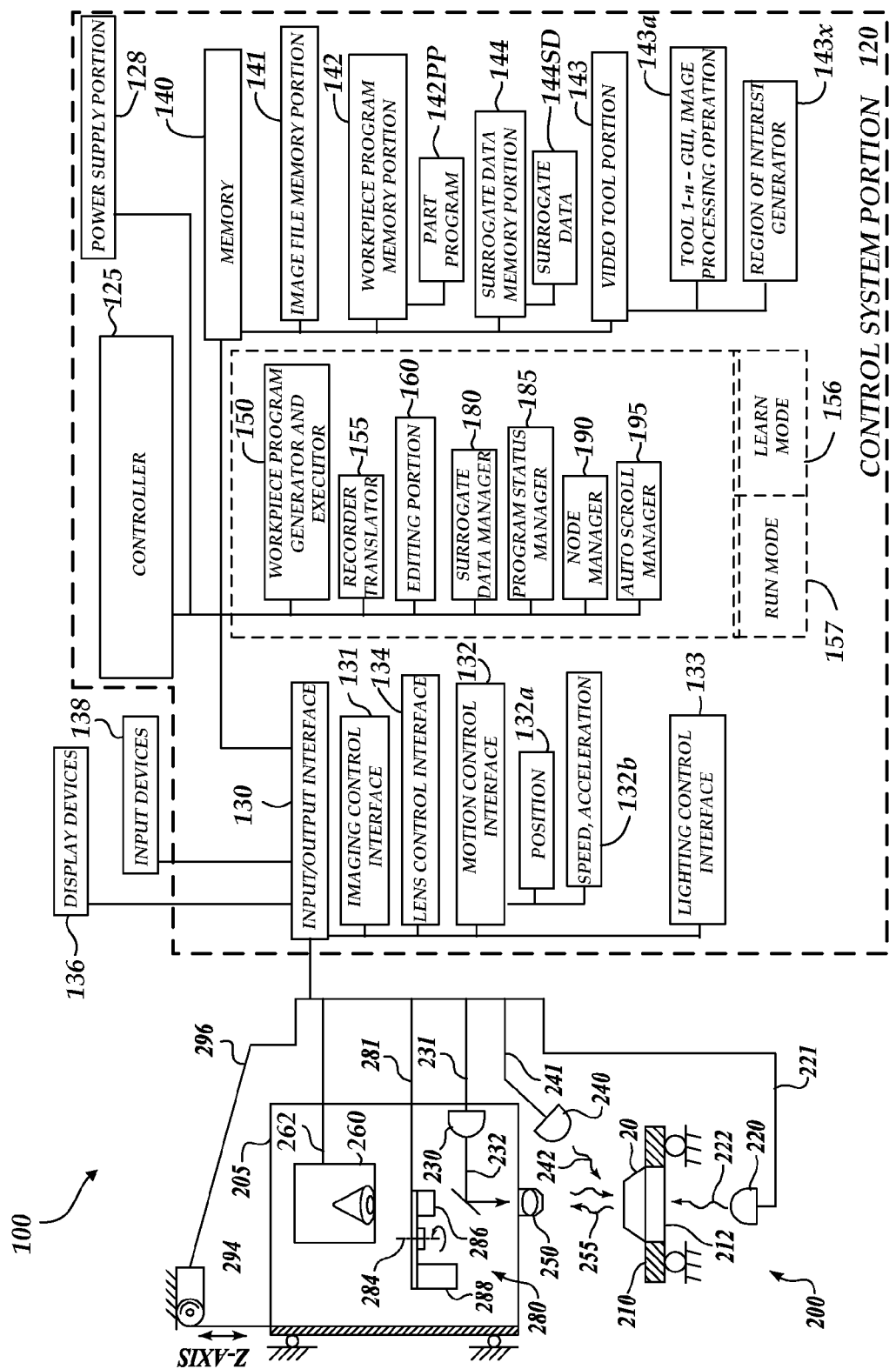
FIGS. 2A and 2B are block diagrams of a control system portion and a vision components portion of a machine vision inspection system similar to that of FIG. 1, and including features usable in various embodiments according to this invention.
Figure 2B:
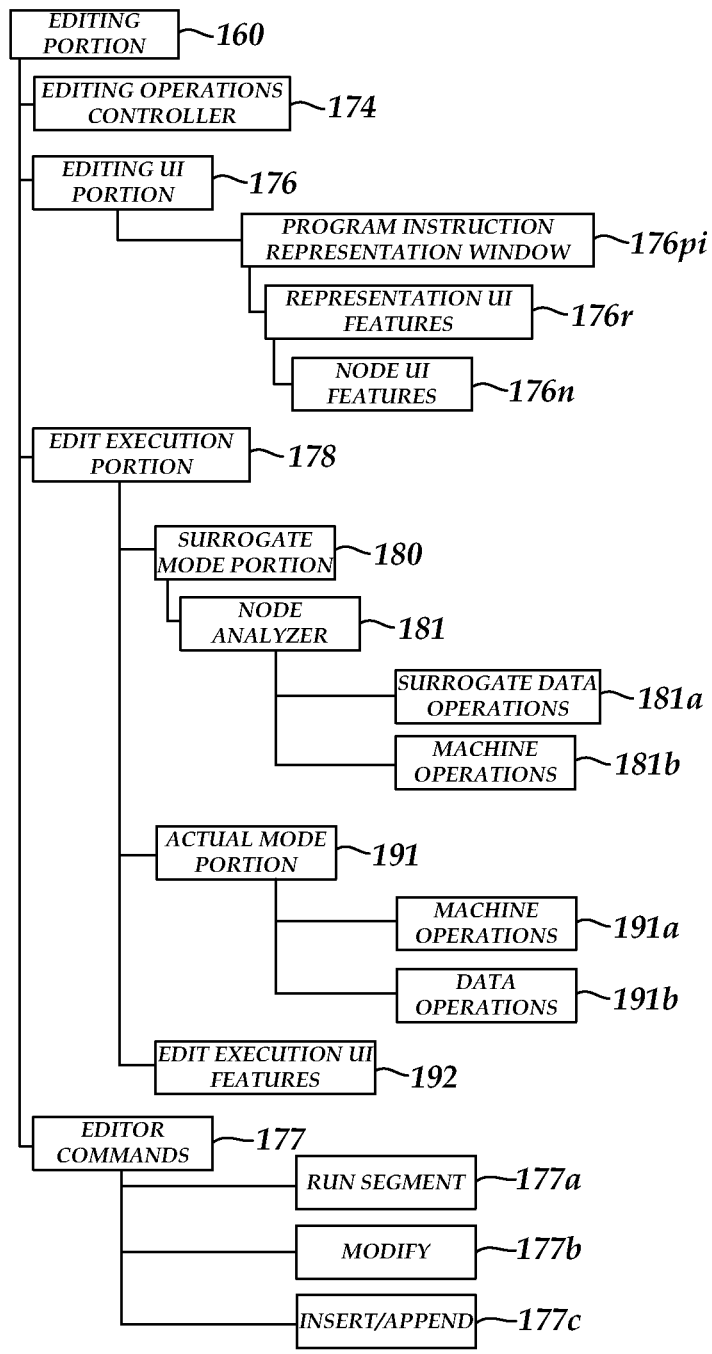

FIGS. 2A and 2B are block diagrams of a control system portion 120 and a vision components portion 200 of a machine vision inspection system 100 similar to the machine vision inspection system of FIG. 1, and including features usable in various embodiments according to the present invention. As will be described in more detail below, the control system portion 120 is utilized to control the vision components portion 200. As shown in FIG. 2A, the vision components portion 200 includes an optical assembly portion 205, light sources 220, 230, and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included. The optical assembly portion 205 is controllably movable along a Z-axis that is generally orthogonal to the X and Y axes, by using a controllable motor 294, as described further below.

A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a coaxial light 230, and a surface light 240 may emit source light 222, 232, or 242, respectively, to illuminate the workpiece or workpieces 20. The source light is reflected or transmitted as workpiece light 255, which passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, and 240 may be connected to the control system portion 120 through signal lines or busses 221, 231, and 241, respectively. To alter the image magnification, the control system portion 120 may rotate the turret lens assembly 280 along axis 284 to select a turret lens, through a signal line or bus 281.

In various exemplary embodiments, the optical assembly portion 205 is movable in the vertical Z-axis direction relative to the workpiece stage 210 using a controllable motor 294 that drives an actuator, a connecting cable, or the like, to move the optical assembly portion 205 along the Z-axis to change the focus of the image of the workpiece 20 captured by the camera system 260. The term Z-axis, as used herein, refers to the axis that is intended to be used for focusing the image obtained by the optical assembly portion 205. The controllable motor 294, when used, is connected to the input/output interface 130 via a signal line 296.

As shown in FIG. 2A, in various exemplary embodiments, the control system portion 120 includes a controller 125, a power supply portion 128, the input/output interface 130, a memory 140, a workpiece program generator and executor 150, a recorder translator 155, and a learn mode component 156, a run mode component 157, an editing portion 160, a surrogate data manager 180, a program status manager 185, a node manager 190, and an auto scroll manager 195. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a, and a speed/acceleration control element 132b, although such elements may be merged and/or indistinguishable. The lighting control interface 133 controls, for example, the selection, power, on/off switch, and strobe pulse timing if applicable, for the various corresponding light sources of the machine vision inspection system 100.

The memory 140 includes an image file memory portion 141, a workpiece program memory portion 142 that may include one or more part programs 142PP, or the like, a video tool portion 143, and a surrogate data memory portion 144. The video tool portion 143 includes video tool portion 143a and other video tool portions, which determine the GUI, image processing operation, etc., for each of the corresponding video tools. Many known video tools are included in commercially available machine vision inspection systems, such as the QUICK VISION® series of vision systems and the associated QVPAK® software, discussed above. The video tool portion 143 also includes a region of interest (ROI) generator 143x that supports automatic, semi-automatic, and/or manual operations that define various ROIs that are operable in various video tools included in the video tool portion 143. The surrogate data memory portion 144 includes surrogate data 144SD. As will be described in more detail below, in accordance with the present invention, when editing a part program, rather than being required to execute all of the steps of the part program in order to generate the needed context for continuing edits, certain context can be simulated using previously saved data as surrogate data.

In general, the memory portion 140 stores data usable to operate the vision system components portion 200 to capture or acquire an image of the workpiece 20 such that the acquired image of the workpiece 20 has desired image characteristics. The memory portion 140 may also store inspection result data, may further store data usable to operate the machine vision inspection system 100 to perform various inspection and measurement operations on the acquired images (e.g., implemented, in part, as video tools), either manually or automatically, and to output the results through the input/output interface 130. The memory portion 140 may also contain data defining a user interface operable through the input/output interface 130.

The signal lines or busses 221, 231, and 241 of the stage light 220, the coaxial light 230, and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various user interface features that are usable to perform inspection operations, and/or to create and/or modify part programs, to view the images captured by the camera system 260, and/or to directly control the vision system components portion 200. In particular, according to various exemplary embodiments of the present invention, the display devices 136 and input devices 138 are used to present various user interface features usable to allow rapid, efficient, intuitive, and flexible editing of part programs on the machine vision inspection system 100.

The workpiece generator and executor 150, recorder translator 155, learn mode executor 156, run mode executor 157, editing portion 160, surrogate data manager 180, program status manager 185, node manager 190 and auto scroll manager 195 may in one embodiment all be considered to be part of a general machine controller block MC that is linked to the controller 125. The workpiece program generator and executor 150 is responsible for creating and executing part programs. It will be appreciated that the terms "workpiece program" and "part program" may be used interchangeably herein. In accordance with the operations of the workpiece program generator and executor 150, in various exemplary embodiments, when a user utilizes the machine vision inspection system 100 to create a part program for the workpiece 20, the user generates part program instructions either by explicitly coding the instructions automatically, semi-automatically, or manually, using a workpiece programming language, and/or by generating the instructions by operating the machine vision inspection system 100 in a learn mode (e.g., as controlled by the learn mode portion 156) to provide a desired image acquisition training sequence. For example a training sequence may comprise positioning a workpiece feature in the field of view (FOV), setting light levels, focusing or autofocusing, acquiring an image, and providing an inspection training sequence applied to the image (e.g., using video tools). The learn mode operates such that the sequence(s) are captured or recorded and converted to corresponding part program steps (i.e., instructions). These part program steps, when the part program is executed in a run mode (e.g., as controlled by the run mode portion 157), will cause the machine vision inspection system to reproduce the trained image acquisition and inspection operations to automatically inspect a workpiece or workpieces matching the workpiece used when creating the part program.

The recorder translator 155 is utilized for translating machine operations into part program code. In other words, if a user performs an action (e.g., such as altering a video tool that is used to measure a feature on a workpiece) a basic instruction is generated that is translated into a machine readable language, and a reverse translation may also be performed. As will be described in more detail below, in certain embodiments of the present invention, certain mark up type language instructions in a part program may also be translated into instruction representations in a user interface. In one specific example embodiment, the mark-up language code may be XML-like code. The editing portion 160 provides or activates various operations and user interface features related to editing a part program, as will be described in more detail below with respect to FIG. 2B.

The surrogate data manager 180 links to surrogate data, which in accordance with the present invention, may be recorded in a part program. In certain implementations, the surrogate data manager 180 is responsible for obtaining the surrogate data from an output where it would normally be generated, and providing the surrogate data to be written into the part program. The program status manager 185, in one embodiment, manages whether programs are protected or unprotected. In one implementation, an unprotected part program may include stored surrogate data, while a protected part program has had any surrogate data removed. In one example embodiment, protected programs are programs for which the editing process has been completed, such as may be utilized in a factory in a run mode. In one embodiment, a user may select a part program that is to be protected, at which point the program status manager 185 automatically removes all of the surrogate data so that the part program is not burdened with extra execution steps at run time. The program status manager 185 is also responsible for when a program is unprotected, such that the surrogate data remains recorded in the part program and when a part program is recalled by the editing portion 160, the surrogate data is indicated as being available.

In one embodiment, the node manager 190 is responsible for managing node numbers that are assigned to nodes in a part program. In one implementation, within a representation of a part program, each of the instruction representations is assigned a node number. In certain implementations, an organizational tree structure may be utilized wherein there are parent nodes and child nodes. In certain implementations, every line of a part program representation that is generated by the recorder translator 155 is assigned a node number by the node manager 190. The auto scroll manager 195 utilizes the node numbers assigned by the node manager 190 to display related elements of associated part program elements and corresponding editing functions in different windows at the same time. In other words, if a user wishes to see which measurements of a workpiece are related to which instruction representations and coded instructions in a part program, the auto scroll manager 195 will automatically scroll in the respective windows to the relevant lines in the part program representation and/or coded instructions that correspond to the relevant node number.

Related editing features and functions are also described in patent applications entitled "Machine Vision System Program Editing Environment Including Synchronized User Interface Features" (61/560,278); "System and Method Utilizing An Editing Initialization Block In A Part Program Editing Environment In A Machine Vision System" (Ser. No. 13/297,182); and "Machine Vision System Editing Environment For A Part Program In Which A Continuous Stream Of Image Acquisition Operations Are Performed During A Run Mode" (Ser. No. 13/297,220), each of which is filed concurrently herewith and hereby incorporated by reference.

FIG. 2B illustrates additional components of the editing portion 160 of FIG. 2A. As shown in FIG. 2B, the editing portion 160 includes an editing operations controller 174, an editing user interface portion 176, an editor commands portion 177 and an edit execution portion 178. The editing operation controller 174 controls the operations for the editing functions, and the editing user interface portion 176 provides the user interface features for the editing functions. The editing user interface portion 176 includes a program instruction representation window 176PI, which includes representation user interface features 176R, which includes node user interface features 176N. The program instruction representation window 176PI provides a part program representation, as will be described in more detail below with respect to FIG. 3. In one embodiment, the part program representation may be provided in a tree structure. The representation user interface features 176R provides features such as an insertion pointer which may change color depending on the state of the context and how the context was obtained (e.g., whether the context was produced from surrogate data, by an actual run, etc.). With regard to the node user interface features 176N, in one embodiment these may include features such as icons or broken icons, and color highlights, so as to indicate if a node is active, etc.

The edit execution portion 178 is responsible for various execution modes during an editing process, and includes a surrogate mode portion 180, an actual mode portion 191, and an edit execution user interface features portion 192. The surrogate mode portion 180 includes a node analyzer 181, which includes surrogate data operations 181A and machine operations 181B. As will be described in more detail below, when the surrogate mode portion 180 operates a surrogate execution mode, in accordance with the present invention, surrogate data is utilized for generating context for the continuing editing operations. The node analyzer 181 in one implementation determines whether the part program execution has reached the target node (e.g., where a modification is to be made in the part program). The node analyzer 181 determines whether the surrogate data operations 181A or actual machine operations 181B will be performed, in accordance with the type of node that is involved. In general, once the target node is reached, then actual machine operations are performed, wherein for part program instructions prior to the target node, surrogate data operations may be utilized for generating at least some of the context that is needed for the continuing editing operations. If surrogate data is missing, a user may be prompted to allow/perform actual machine operations to generate the needed context. In one implementation, each node is analyzed to determine if surrogate data operations are applicable, including whether surrogate data exists, if it is the right type of node for surrogate data operations, or alternatively, whether actual machine operations need to be utilized, etc.

The actual mode portion 191 includes operations that are more traditionally performed by prior machine vision systems. It will be appreciated that the actual mode portion 191 may also be called by the surrogate mode portion 180 for performing the machine operations 181B, when appropriate. The actual mode portion 191 includes machine operations 191A and data operations 191B. The machine operations 191A perform actual machine operations (e.g., moving the stage as part of a video tool operation), while the data operations 191B generally output data. The edit execution user interface features 192 provide user interface features for the execution of the editing functions (e.g., indications as to the status of various execution operations, such as color codes indicating what portions of a part program have utilized surrogate data, or have been run through an actual execution, etc.).

The editor commands 177 includes a run segment portion 177A, a modify portion 177B and an insert/append portion 177C. The operations of the insert/append portion 177C will be described in more detail below with respect to FIGS. 6-8, while the operations of the modify portion 177B will be described in more detail below with respect to FIGS. 9-11B. In general, the run segment portion 177A performs an actual run of a selected segment of the part program. It will be appreciated that in order to run a selected segment of a part program, the proper context up to the selected segment must be established. As will be described in more detail below, in accordance with the present invention, the proper context may be established by utilizing surrogate data. If surrogate data does not exist for a certain portion of a part program, then a segment may be run so as to generate the needed surrogate data. It will be appreciated that in prior machine vision systems, it has been difficult to run an isolated segment of a part program without running all of the preceding portions of the part program, due to the need for the proper context leading up to the selected segment. For example, if the segment required the stage to be lowered, but the system was unaware of the present X-Y-Z location of the stage, then lowering the stage to an unknown position could be inadvisable. Thus, in prior implementations, the technique typically utilized was to run the entire part program from the beginning in order to be able to run a segment in the middle, for which all of the preceding operations could require a significant amount of time to perform. In contrast, in accordance with the present invention, surrogate data may be utilized to establish the proper context for making edits to or running a segment of a part program without requiring the running of the entire part program from the beginning.

The modify portion 177B has certain similarities to the operation of the run segment portion 177A. In general, when an instruction representation in a part program is selected to be modified, then the surrogate mode may be utilized for the portions of the part program that precede the instruction that is to be modified. In one embodiment, when the modify command is selected for an instruction representation in a part program, the node for the instruction representation is designated as the target node. Once the target node is reached, the editor switches out of the surrogate mode and switches into the actual execution mode (e.g., as controlled by the actual mode portion 191) and executes the first relevant part program instruction of the node. In one embodiment, if the instruction that is selected for modification corresponds to a child node, then the actual execution may be designated to begin at the parent node. In one specific example embodiment, if a child node related to a box tool is to be modified, the parent node, which involves setting up the image acquisition for the box tool, may be the node at which the actual execution is set to begin. With regard to the insert/append component 177C, if the insert is in between child nodes, then the parent node may also need to be executed in order to perform the desired insertion. It will be appreciated that in certain implementations an append operation may generally be considered to be a special case of an insert operation, which occurs at the end of an existing part program.

Figure 3:
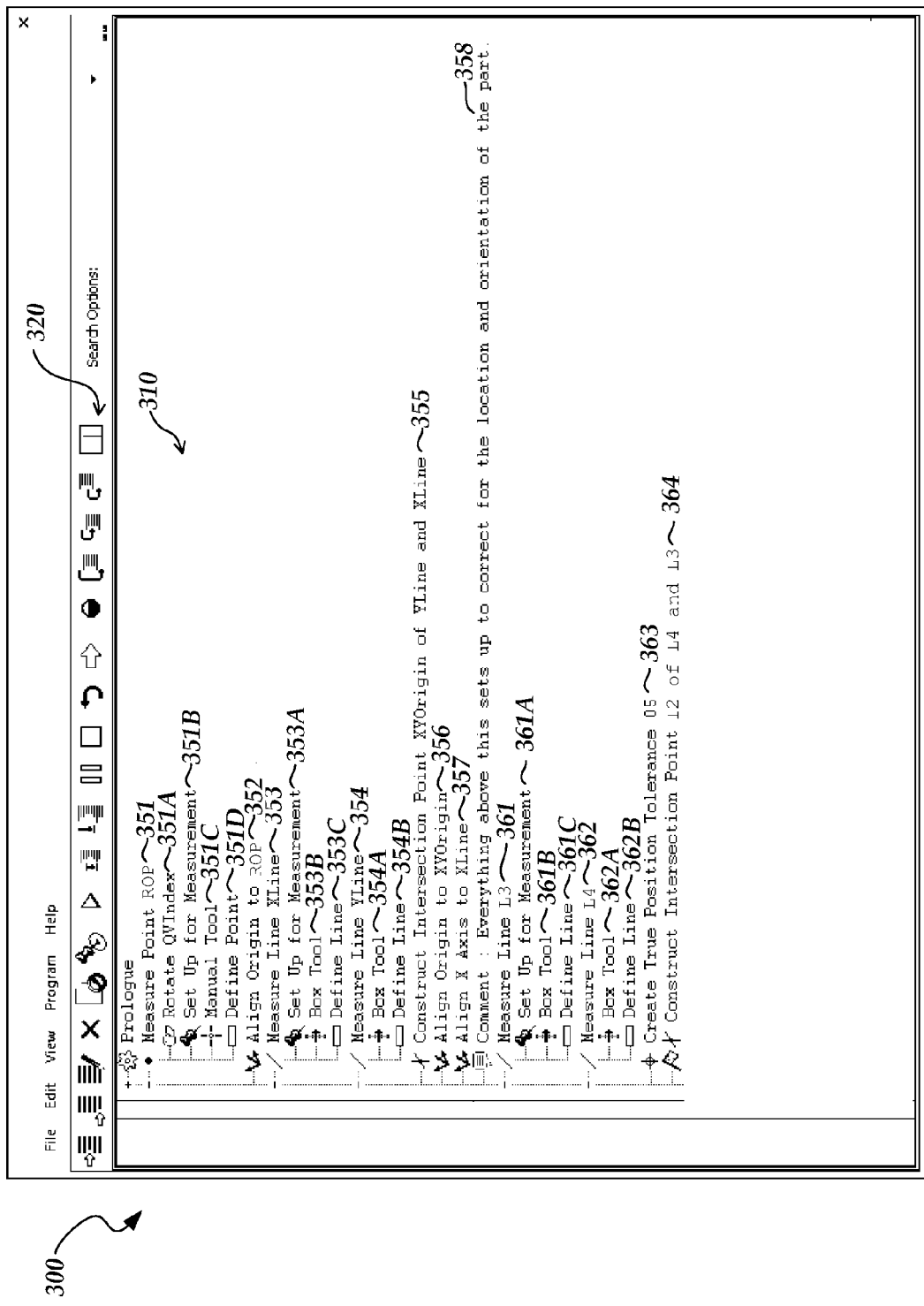
FIG. 3 is a diagram of an editing interface including a part program representation that has a plurality of instruction representations.

FIG. 3 is a diagram of an editing interface 300 including a representation of a part program 310 that has a plurality of initial part program instruction representations 351-364. The editing interface 300 also includes various measurement and/or operation selection bars such as the selection bar 320. The operation of the specific instruction representations of the part program representation 310 will be described in more detail below with respect to FIG. 4.

Figure 4:
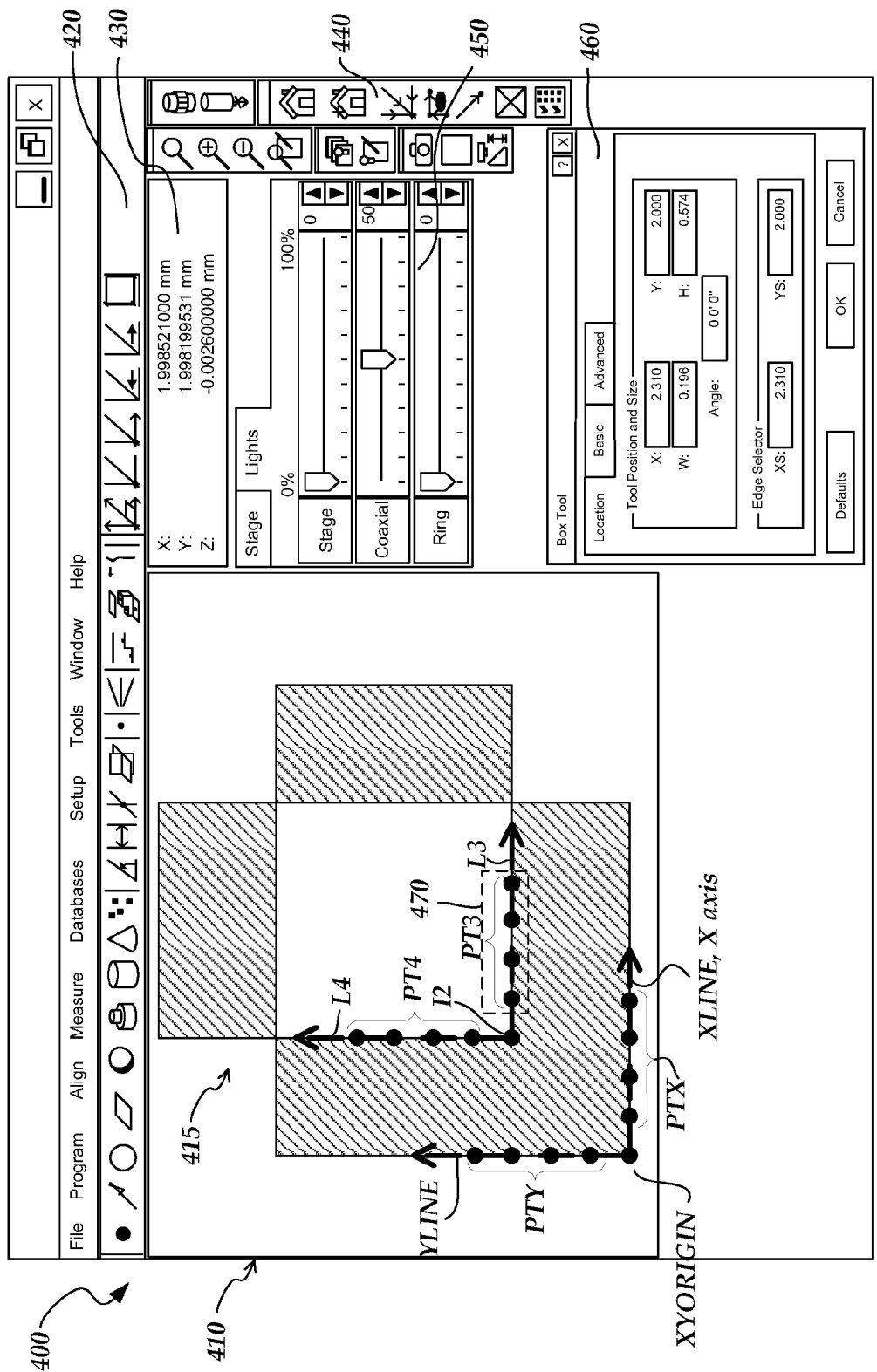
FIG. 4 is a diagram of a user interface including an image of a workpiece on which the part program corresponding to FIG. 3 has been performed.

FIG. 4 is a diagram illustrating a user interface 400 including an image of a field of view window 410 with a workpiece 415, on which the part program corresponding to FIG. 3 has been performed. The user interface 400 also includes various measurement and/or operation selection bars such as the selection bars 420 and 440, a real-time X-Y-Z (position) coordinate window 430, a light control window 450, and a video tool parameter box 460. As will be described in more detail below, various features on the workpiece 415 are determined in accordance with related part program instruction representations of FIG. 3, such as sets of edge points PTX, PTY, PT3 and PT4, lines XLINE, YLINE, L3 and L4, an origin point XYORIGIN, and an intersection point I2.

The following description will make reference to both the initial part program instruction representations 351-364 of FIG. 3, and the corresponding features on the workpiece 415 of FIG. 4. In one embodiment, each of the instruction representations 351-364 is associated with a node, and is assigned a node number. In certain implementations, a tree-structure is utilized, wherein some of the instruction representations are associated with parent nodes, and some are associated with children nodes. For example, the children node instruction representations 351A-351D, 353A-353C, 354A-354B, 361A-361C, and 362A-362B are associated with parent node instruction representations 351, 353, 354, 361, and 362, respectively. It will also be appreciated that in one embodiment, the instruction representations 351-364 as displayed in the editing interface 300, comprise icons and labels derived from the mark-up language instructions of the part program. In one embodiment, the mark-up language of the part program may comprise XML-like code. The instruction representations 351-364 thus point to associated code instructions that are executed, as will be described in more detail below with respect to FIGS. 5A and 5B.

As shown in FIG. 3, the part program representation 310 begins with the instruction representations 351 and 352, which indicate that the user manually selects a location on the workpiece 415 to act as a rough origin point ROP (not shown), and then aligns the origin to the rough origin point ROP. More specifically, the instruction representations 351A, 351B, 351C, and 351D indicate that the user sets up and utilizes a manual tool to define the rough origin point ROP and the instruction representation 352 aligns the origin with the rough origin point ROP. The instruction representation 353 then indicates that a box tool will be opened for measuring the line XLINE. More specifically, the instruction representations 353A and 353B indicate that the user sets up (e.g., including moving the stage to a designated location and acquiring a corresponding image) and utilizes the box tool to determine the edge points PTX. The functions and operations of box tools and other edge detection video tools are known in the art and are described in more detail in the previously incorporated references. The edge points PTX that are determined by the box tool are then utilized by the instruction representation 353C to define the line XLINE. Similarly, the instruction representation 354 indicates that a box tool will be opened for measuring the line YLINE, wherein the instruction representation 354A indicates that the user utilizes the box tool to determine the edge points PTY, which are then utilized as indicated by the instruction representation 354B to define the line YLINE.

The instruction representation 355 then indicates that an intersection point XYORIGIN is determined at the intersection of the lines XLINE and YLINE. The instruction representation 356 then indicates that the machine vision system is commanded to align the origin to the point XYORIGIN. The instruction representation 357 then indicates that the machine vision system is commanded to align the X axis for the workpiece 415 to the line XLINE. As will be described in more detail below with respect to FIG. 5, and as indicated by the comment line 358, the operations of the instruction representations 351-357 establish the correct location and orientation of the workpiece 415 for performing additional measurements.

The instruction representation 361 then indicates that a box tool will be opened for measuring the line L3. More specifically, the instruction representations 361A and 361B indicate that the user sets up (e.g., including moving the stage to a designated location and acquiring a corresponding image) and utilizes the box tool to determine the edge points PT3, which are then utilized as indicated by the instruction representation 361C to define the line L3. As will be described in more detail below, the box tool utilized for measuring the line L3 (i.e., illustrated as box tool 470 in FIG. 4), and the associated instruction representations 361 and 361A-361C, are utilized as examples in FIGS. 5A and 5B and 9-11B for illustrating how surrogate data is generated, stored and modified.

Returning to FIG. 3, the instruction representation 362 indicates that a box tool will be opened for measuring the line L4, wherein the instruction representation 362A indicates that the user utilizes a box tool to determine the edge points PT4, which are then utilized as indicated by the instruction representation 362B to define the line L4. The instruction representation 363 indicates that the user defines a selected position tolerance and the instruction representation 364 indicates that an intersection point I2 is determined where the previously determined lines L3 and L4 intersect.

After the part program corresponding to the representation 310 is stored and exited, when the part program is recalled for editing, prior implementations have required that the entire part program be executed from the beginning, in order to produce valid context for continuing edits to the part program. While prior implementations have produced accurate results and part programs by executing all of the instructions each time a part program is recalled for editing, the execution of all of the instructions may take a significant amount of time (particularly those instructions that require certain time consuming processes such as hardware interactions, etc.). As will be described in more detail below, in accordance with the present invention, rather than executing the entire part program from the beginning, previously saved data may be used as surrogate data for simulating valid context for continuing edits to the part program.

In other words, in one embodiment, when continuing edits are being made to the part program for making measurements on the workpiece 415, it is useful to know certain parameters. For example, in order to know the correct thresholds, size, and location for a video tool, it is necessary to have the right video image, including information such as the correct stage position, light levels, magnification, etc. In one embodiment, such information may be considered as part of the "hardware context." In addition, in order to know if a sequence is correct for continuing edits to the part program, it is useful to know what has been done already, including what features have been measured, what part coordinate system is being utilized, etc. In one embodiment, this information may be considered as part of the software context. In one embodiment, the context is generally considered as establishing the user interface of the machine vision inspection system in a state such that all of the native interface control elements are ready for modifying the part program. As noted above, accurate context is provided at the time the part program is initially recorded, and also later at runtime, in that all of the part program instructions (e.g., corresponding to the representations 351-364) are generally executed in order. As noted above, this provides a valid context for continuing edits to the part program, including indicating any measurements and results already produced by the part program (e.g., the indications of the lines XLINE, YLINE, L3, L4, and intersection points XYORIGIN and I2 as illustrated with respect to the workpiece 415 in the user interface 400).

As will be described in more detail below, in accordance with the present invention, when editing a part program, rather than being required to execute all of the instruction representations of the part program in order to generate the needed context, certain context can be simulated by using previously saved data as surrogate data. Briefly, during the recording or runtime execution of a part program, the data that is needed to determine context is stored with the part program. Then, at a later time, certain results may be simulated utilizing the saved data as surrogate data in order to produce the desired context. Thus, by avoiding the execution of certain time-consuming operations (e.g., those requiring hardware interaction such as the moving of the stage, edge detection, focusing, lighting changes, pattern matching, etc.), significant time savings may be achieved. The saving of data that may be later utilized as surrogate data will be described in more detail below with respect to FIGS. 5A and 5B.

FIGS. 5A and 5B are diagrams 500A and 500B of mark-up language code instructions which correspond to some of the instruction representations of the part program representation of FIG. 3. More specifically, FIGS. 5A and 5B show the part program instructions in XML-like code which correspond to the instruction representations 361 and 361A-361C of FIG. 3 for measuring the line L3. It will be appreciated that in one embodiment the instruction representations 361 and 361A-361C comprise icons and labels that are derived from the XML-like code instructions of FIGS. 5A and 5B. The instruction representations 361 and 361A-361C are not themselves executed, but instead point to the associated code instructions of FIGS. 5A and 5B that are executed.

As shown in FIGS. 5A and 5B, the XML-like code instructions include node I.D. numbers 561, 561A, 561B, and 561C, which in one embodiment may correspond to the instruction representations 361, 361A, 361B, and 361C of FIG. 3. The XML-like code instructions also include certain position information 510 for the image position, and certain box tool position information 520 for the box tool, such as may be displayed in the areas 430 and 460 of the user interface 400 of FIG. 4. As shown in FIG. 5B, data 530 is stored with the part program that may be utilized at a later time as surrogate data for simulating context (e.g., as will be described in more detail below with respect to FIGS. 6-8). More specifically, when the instruction representation 361B of FIG. 3 indicates that the box tool 470 of FIG. 4 is run to determine the set of edge points PT3, the positions of the set edge points PT3 relative to the part coordinate system for the workpiece are stored in the XML-like code instructions as the data 530. As will be described in more detail below with respect to FIGS. 11A and 11B, modifications may be made to the part program which may result in modifications to the surrogate data 530.

Figure 6:
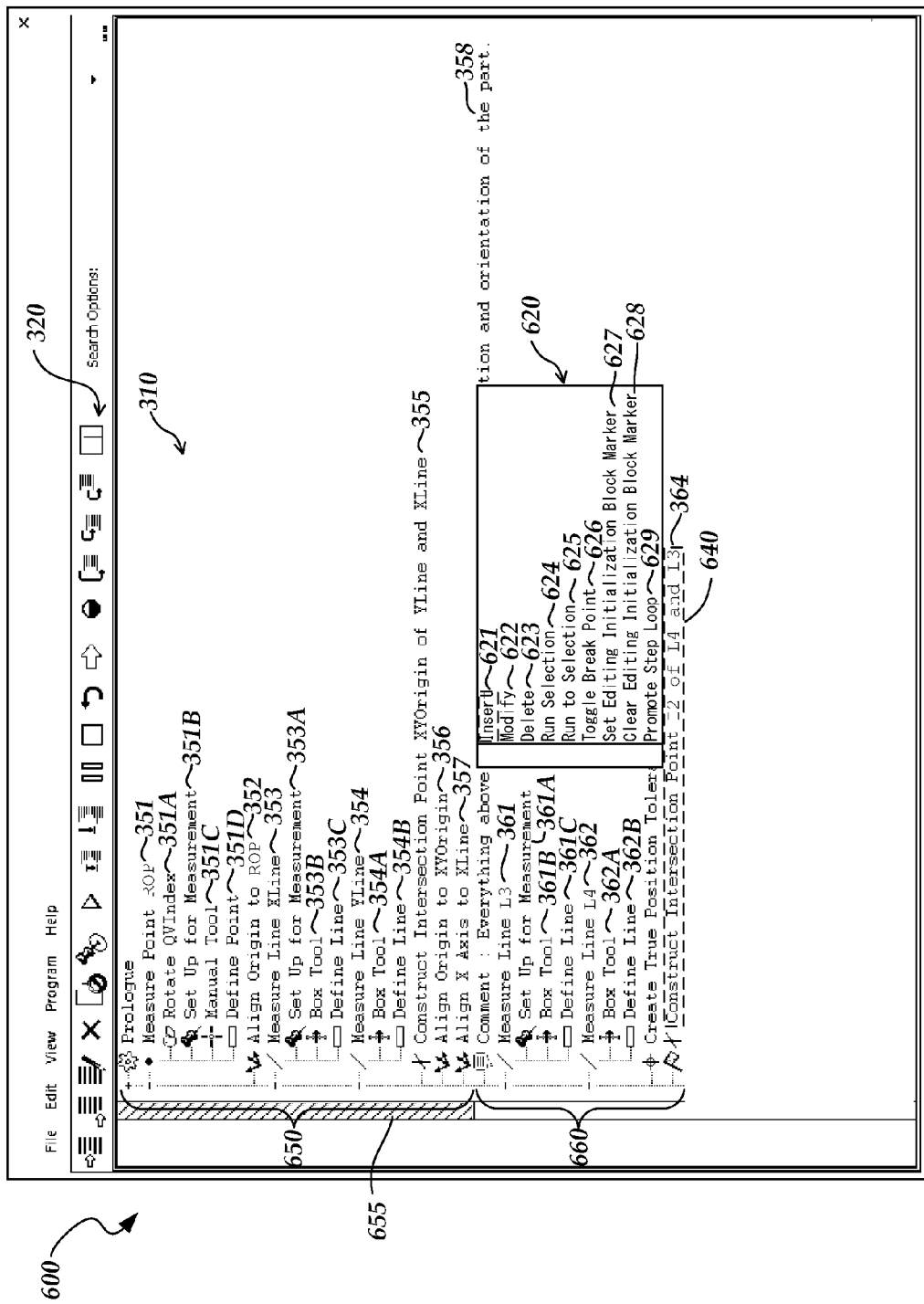
FIG. 6 is a diagram of an editing interface including the part program representation of FIG. 3 and further including a drop down menu for performing edit mode commands or functions such as inserting instructions in the part program.

FIG. 6 is a diagram of an editing interface 600 including the part program representation 310 of FIG. 3 and further including a drop down menu 620 for performing various edit mode commands or functions such as inserting instructions into the part program. As shown in FIG. 6, the drop down menu 620 includes a selection 621 for performing an insert operation, a selection 622 for performing a modify operation, a selection 623 for performing a delete operation, a selection 624 for performing a run selection operation, a selection 625 for performing a run to selection operation, a selection 626 for performing a toggle breakpoint operation, a selection 627 for performing a set editing initialization block marker operation, a selection 628 for performing a clear editing initialization block marker operation, and a selection 629 for performing a promote step loop operation. In one embodiment, the drop down menu 620 may be provided when a user selects a particular instruction representation (e.g., in the illustration of FIG. 6, the user has selected the last instruction representation 364 by using a mouse to move a selector over the instruction representation 364 and then by right clicking on it). The instruction representation that is selected (e.g., instruction representation 364) may be indicated by a selector box (e.g., a selector box 640 as illustrated in FIG. 6), or highlighting or other indicator method. As will be described in more detail below with respect to FIGS. 7 and 8, once a user selects an instruction representation (e.g., instruction representation 364) and an editing operation from the drop down menu 620 (e.g., the selection 621 for an insert operation), then previously saved data (e.g., data 530 of FIG. 5B) may be utilized as surrogate data for establishing a valid context for the selected edits to the part program. In addition to the selections from the drop down menu 620 for editing operations, the selection 627 may be utilized for establishing an editing initialization block, which can help ensure the accuracy of the context that is simulated by utilizing the surrogate data.

As described in concurrently filed and commonly assigned application entitled "System and Method Utilizing an Editing Initialization Block in a Part Program Editing Environment in a Machine Vision System," Ser. No. 13/297,182, which was previously incorporated by reference, the user may designate one of the instruction representations (e.g., instruction representation 357) as an editing initialization block marker. Once the user designates the instruction representation 357 with the editing initialization block marker, this designates that all of the instruction representations preceding and up to instruction representation 357 (i.e., instruction representations 351-357) are editing initialization instruction representations which make up an editing initialization block 650. The instruction representation 357 is therefore determined to be the last initial part program instruction representation that is an editing initialization step. In one embodiment, an editing initialization indicator may be provided in the editing interface 600 that indicates that each of the instruction representations 351-357 are editing initialization steps. In the specific example illustration of FIG. 6, a color bar 655 (shown with cross hatching) is provided next to the instruction representations 351-357 to indicate that they are in the editing initialization block 650. In alternative embodiments, other editing initialization indicators may be utilized for indicating the editing initialization instruction representations (e.g., a delimiting pointer, delineating markers, highlighting of the actual instruction representations rather than a bar next to the steps, etc.). In one embodiment, when the part program is saved, the indication of which instruction representations are editing initialization instruction representations is also saved.

It will be appreciated that the remaining initial part program instruction representations 361-364 which follow the editing initialization block 650 and which are therefore not included in the editing initialization block, may not be run in the same manner when the editing initialization block is run, as will be described in more detail below. In one embodiment, the instruction representations 361-364 are designated as being in a remaining instruction representations block 660.

As will be described in more detail below, in one embodiment the editing initialization block 650 may be utilized to address certain changes in conditions that may occur during the editing process for a part program. For example, if after a user saves a part program, the user leaves the work station and returns at a later time, in the interim certain changes may have occurred (e.g., the part being inadvertently moved on the stage, etc.) that may affect the editing of the part program. However, due to the amount of time that may be required for rerunning all of the previous instructions of a part program (particularly those instructions that require certain time consuming processes such as hardware interactions, etc.), a user may desire to only rerun certain instructions which help ensure the accuracy of context that is simulating using surrogate data. The editing initialization instruction representations of the editing initialization block 650 represent initial part program instructions that will reestablish a part coordinate system for the part, so as to compensate for any inadvertent movement of the part on the stage since the last part program instructions were performed.

Figure 7:
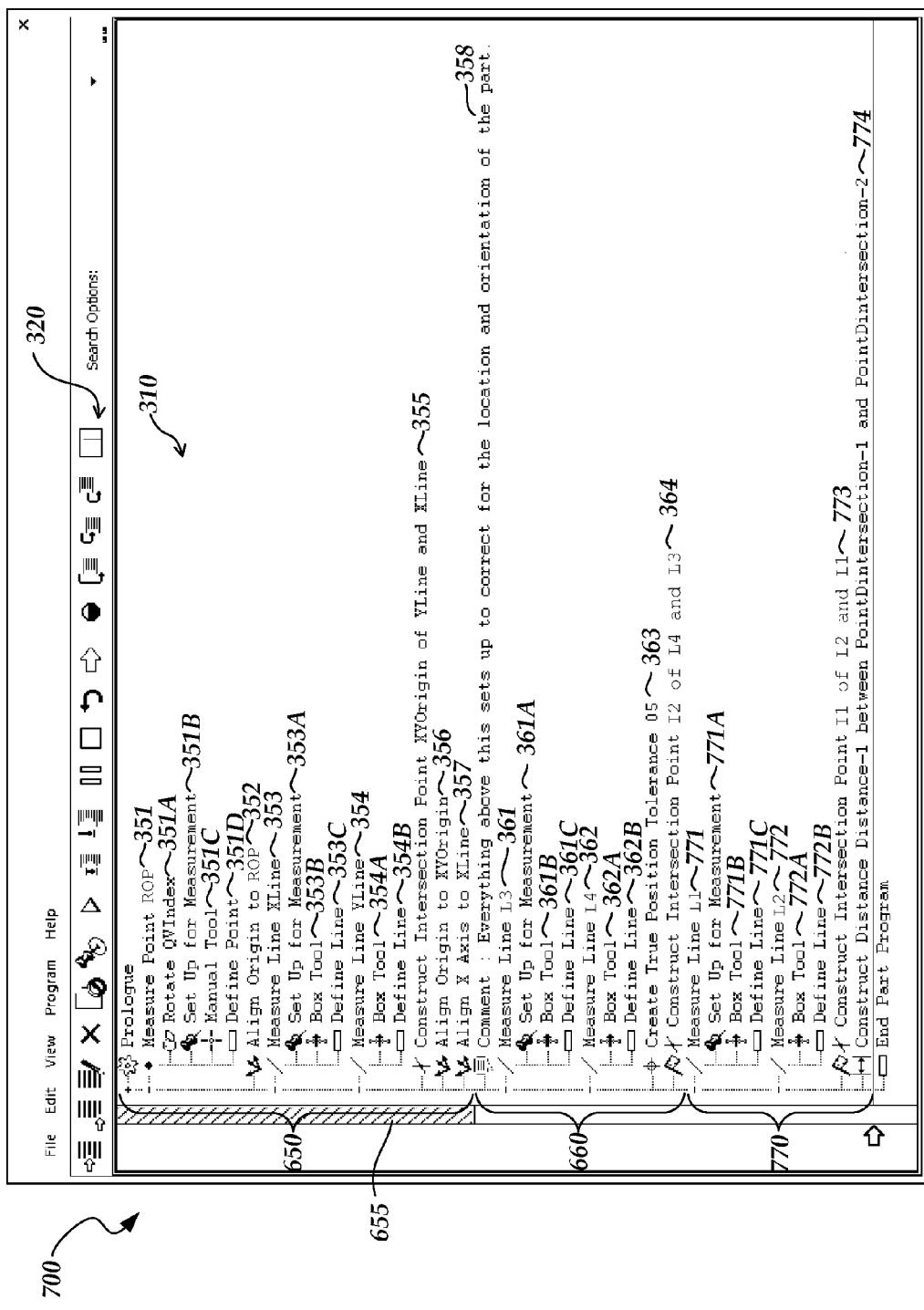
FIG. 7 is a diagram of an editing interface including the part program representation of FIG. 3 and further including additional part program instruction representations that have been inserted or appended at the end of the part program representation.

FIG. 7 is a diagram of an editing interface 700 including the part program representation 310 of FIG. 3 and further including an added instruction representations block 770. The added block 770 includes additional part program instruction representations 771-774 that have been inserted (or appended) to the part program using the insert operation 621 after the editing initialization block 650 has been run. The specific aspects of the insert operation 621 will be described in more detail below with respect to FIG. 8.

Figure 8:
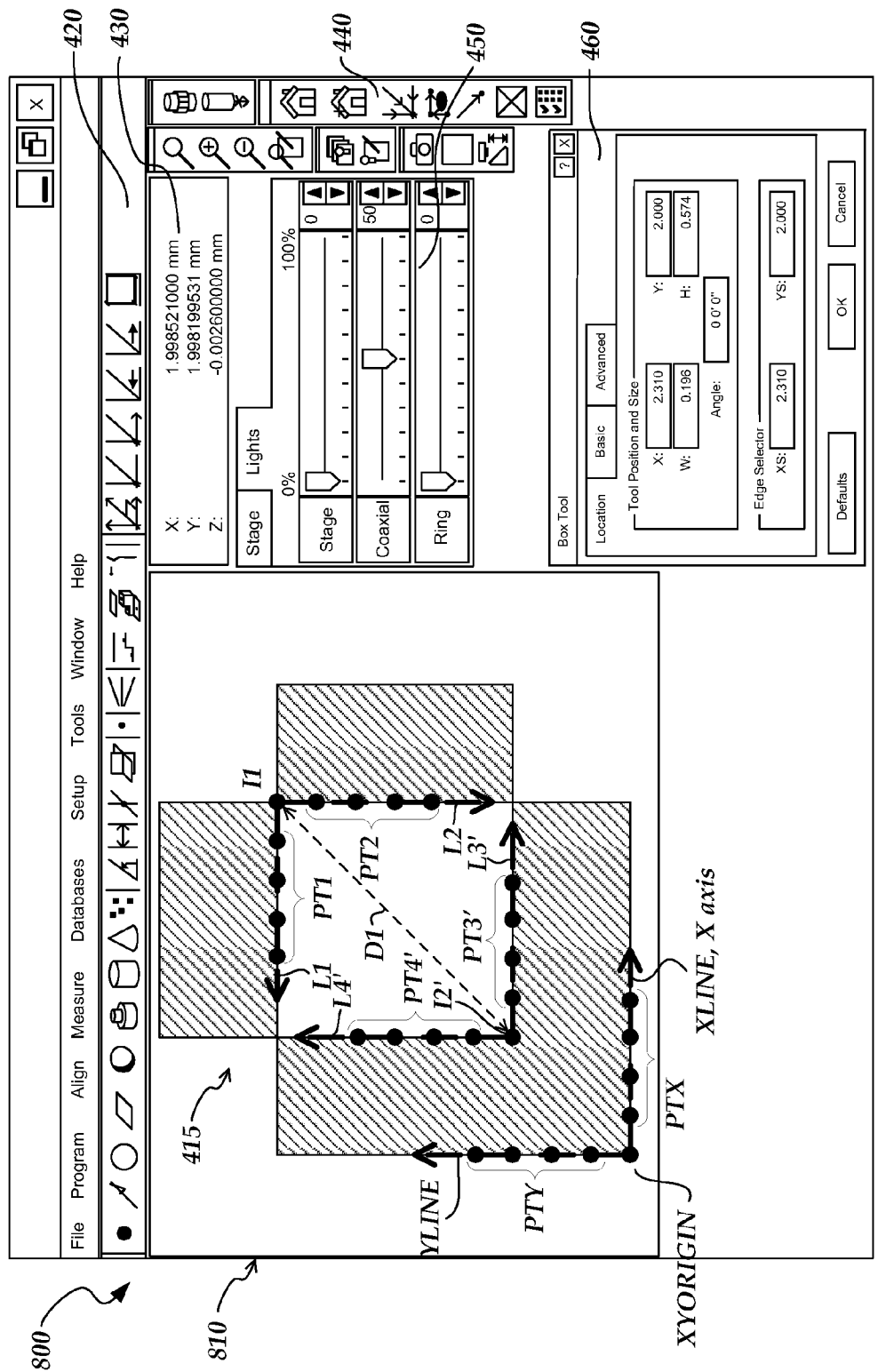
FIG. 8 is a diagram of a user interface including an image of a workpiece on which the part program corresponding to FIG. 7 has been performed.

FIG. 8 is a diagram of a user interface 800 including an image of the workpiece 415 on which the corresponding part program instructions of FIG. 7 are performed. As shown in FIG. 8, the running of the editing initialization block 650 has reestablished the locations of the lines XLINE and YLINE, and the point XYORIGIN on the workpiece 415. More specifically, the corresponding instructions have been run so as to utilize box tools to reestablish the locations of the edge points PTX and PTY on the workpiece 415, from which the locations of the lines XLINE and YLINE and the point XYORIGIN have been redetermined. In accordance with the initial part program instruction representations 351-357, the correct determination of the locations of these features ensures the accuracy of the location and orientation of the workpiece 415 for purposes of accurately redetermining the part coordinate system. In other words, if the workpiece 415 has been inadvertently moved on the stage since the time when the workpiece program 310 was last saved, the running of the editing initialization block 650 would reestablish the correct location and orientation of the workpiece 415 for the purpose of helping ensure the accuracy of any simulated context that is generated based on surrogate data which references the part coordinate system.

In contrast, in one embodiment, the initial part program instruction representations 361-364 in the remaining instruction representations block 660, which are not editing initialization steps, are not run in the same manner. Instead, in certain implementations, the saved location data (e.g., data 530 of FIG. 5B) may be utilized as surrogate data for determining the locations of the sets of points PT3' and PT4'. In other words, the locations of the sets of points PT3' and PT4' may be provided based on the relative locations of those points as determined from the initial performance of the part program instruction representations 351-364 as illustrated in FIG. 4 (e.g., as saved as the data 530 of FIG. 5B). In other words, the relative locations of the points PT3 and PT4 in FIG. 4 (e.g., as referenced to the part coordinate system including the point XYORIGIN) are saved when the part program is initially performed and saved. Thereafter, when the part program 310 is recalled for editing and the editing initialization block 650 is run so as to reestablish the location of the point XYORIGIN as shown in FIG. 8, rather than also reestablishing the locations of the points PT3 and PT4, the previously saved relative locations to the point XYORIGIN are used as surrogate data to determine the locations of the points PT3' and PT4'.

In other words, the locations of the points PT3' and PT4' may not be based on the running of the instructions associated with the representations 361A, 361B, and 362A, all of which require hardware interaction and edge detection and would take a relatively long time to perform. In one embodiment, any instructions which are not in the editing initialization block and which would generally require certain designated time-consuming operations (e.g., hardware interactions such as moving the stage, edge detection, focusing, lighting changes, pattern matching, etc.) are not performed. Instead, any resulting data (e.g., redetermined edge points, etc.) that would have been provided is based on surrogate data (e.g., the locations of the points PT3' and PT4' relative to the point XYORIGIN). As noted above, orientation of the part coordinate system including the correct location of the point XYORIGIN has been reestablished by running the editing initialization block 650 so as to help ensure the accuracy of any related surrogate data that is used.

It will be appreciated that by not running certain designated time-consuming operations, significant time savings may be achieved. This is due to the fact that such operations may take a relatively long time to perform, particularly in comparison to operations which only require calculations to be performed by the controller of the machine vision system. It will be appreciated that while in the example of FIG. 7 only a few such instruction representations (e.g., instruction representations 361A, 361B, and 362A) of this type have been illustrated, in a more detailed part program, significantly more instruction representations of this type may be utilized, for which the time savings may be significant.

In one embodiment, the instructions associated with the representations 361C and 362B (which do not require relatively time-consuming operations and only require the relatively fast processing of the controller of the machine vision system to utilize the points PT3' and PT4' to establish the locations of the lines L3' and L4') may be executed to generate context. Similarly, the additional instructions associated with the representation 364 (which only require the relatively fast processing of the controller) may also be executed to determine the context including the intersection point I2' at the intersection of the lines L3' and L4'. It will be appreciated that the calculations performed by the instructions associated with the representations 361C, 362B and 364 are all of a type that can be performed relatively quickly on the estimated edge points PT3' and PT4' that are determined from the surrogate data, without requiring significant time or input from the user. Thus, certain instructions associated with the initial part program instruction representations 361-364 in the remaining instruction representations block 660 may also be executed to generate context.

With regard to the additional part program instruction representations 771-774 that are added by the insert operation 621, the specific operations associated with the instruction representations will also be described with respect to FIG. 8. Similar to the instruction representations 351-364, the additional part program instruction representations 771-774 are organized in a tree-structure, wherein children node instruction representations 771A-771C and 772A-772B are associated with parent node instruction representations 771 and 772, respectively. As shown in FIG. 8, the instruction representation 771 indicates that a box tool will be opened for measuring a line L1. More specifically, the instruction representations 771A and 771B indicate that a user sets up (e.g., including moving the stage to a desired location and acquiring a corresponding image) and utilizes the box tool to determine the edge points PT1, which are then utilized as indicated by the instruction representation 771C to define the line L1. Similarly, the instruction representation 772 indicates that a box tool will be opened for measuring a line L2, wherein the instruction representation 772A indicates that the box tool is utilized to determine the edge points PT2, which are then utilized as indicated by the instruction representation 772B to define the line L2.

The instruction representation 773 indicates that an intersection point I1 is determined at the intersection of the lines L1 and L2. The instruction representation 774 indicates that a distance D1 is determined between the intersection point I1 and the intersection point I2' that was determined at the instruction representation 364. It will be appreciated that the instruction representation 774 thus illustrates how a new measurement of the distance between the intersection point I1 and the intersection point I2' may rely on the context generated from the utilization of surrogate data. More specifically, the location of the intersection point I2', which as described above was context that was able to be determined relatively quickly and with a reasonable assurance of accuracy based on the running of the editing initialization block 650, was able to be utilized for the new distance measurement D1 to the intersection point I1.

Figure 9:
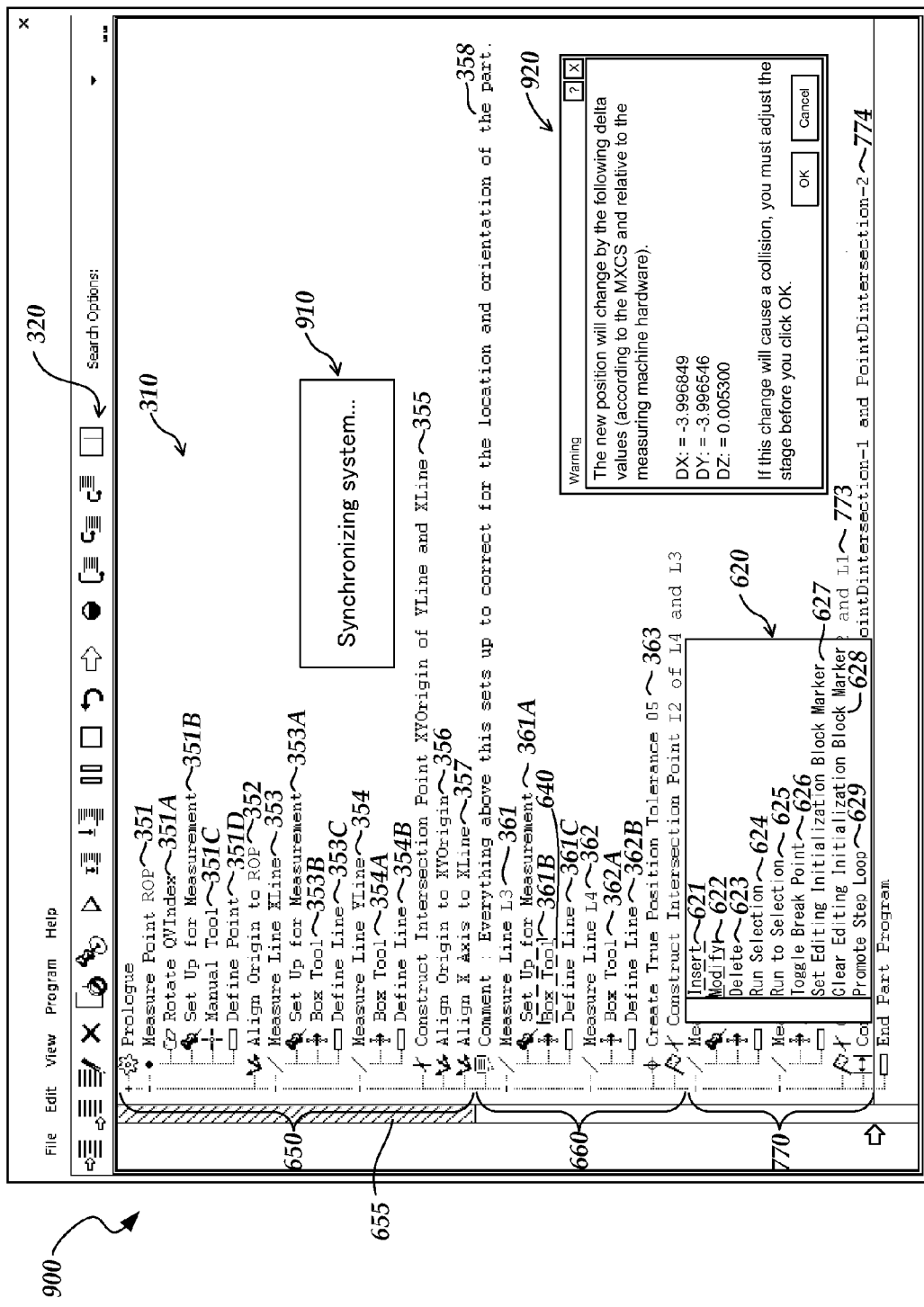
FIG. 9 is a diagram of an editing interface including the part program representation of FIG. 7 and further including a drop down menu for performing edit mode commands or functions such as modifying instructions in the part program, and a query box that asks if the user approves of a corresponding movement of the stage.

FIG. 9 is a diagram of an editing interface 900 including the part program representation of FIG. 7 and further including a drop down menu 620 for performing edit mode commands or functions such as modifying instructions in the part program, and a query box 920 that asks if the user approves of a corresponding movement of the stage. It will be appreciated that the drop down menu 620 is similar to the one described above with respect to FIG. 6. As shown in FIG. 9, the drop down menu 620 has been provided due to a user selecting an instruction representation (e.g., in the illustration of FIG. 9, the user has selected the instruction representation 361B by using a mouse to move a selector over the instruction representation 361B and by right clicking on it). The instruction representation 361B is indicated as the one that is selected by a selector box (e.g., a selector box 640 as illustrated in FIG. 9), or highlighting or other indicator method.

After the user has selected the instruction representation 361B, as a result, the drop down menu 620 is provided, in which the user has selected the modify operation 622. As will be described in more detail below, once the user selects a modify operation 622, a determination is made that the stage will need to be moved. As a result, an indicator box 910 is provided indicating that the system will need to be synchronized, and a query box 920 is provided that asks the user to approve the corresponding movement of the stage.

As will be described in more detail below, the selected instruction representation (e.g., instruction representation 361B) is utilized for the designation of a target node. For certain of the instruction representations which precede the target node, surrogate data may be utilized for determining valid context. Once the target node is reached, then actual execution operations may begin, which may require certain physical operations to be performed, such as requiring a movement of the stage.

Figure 10A:
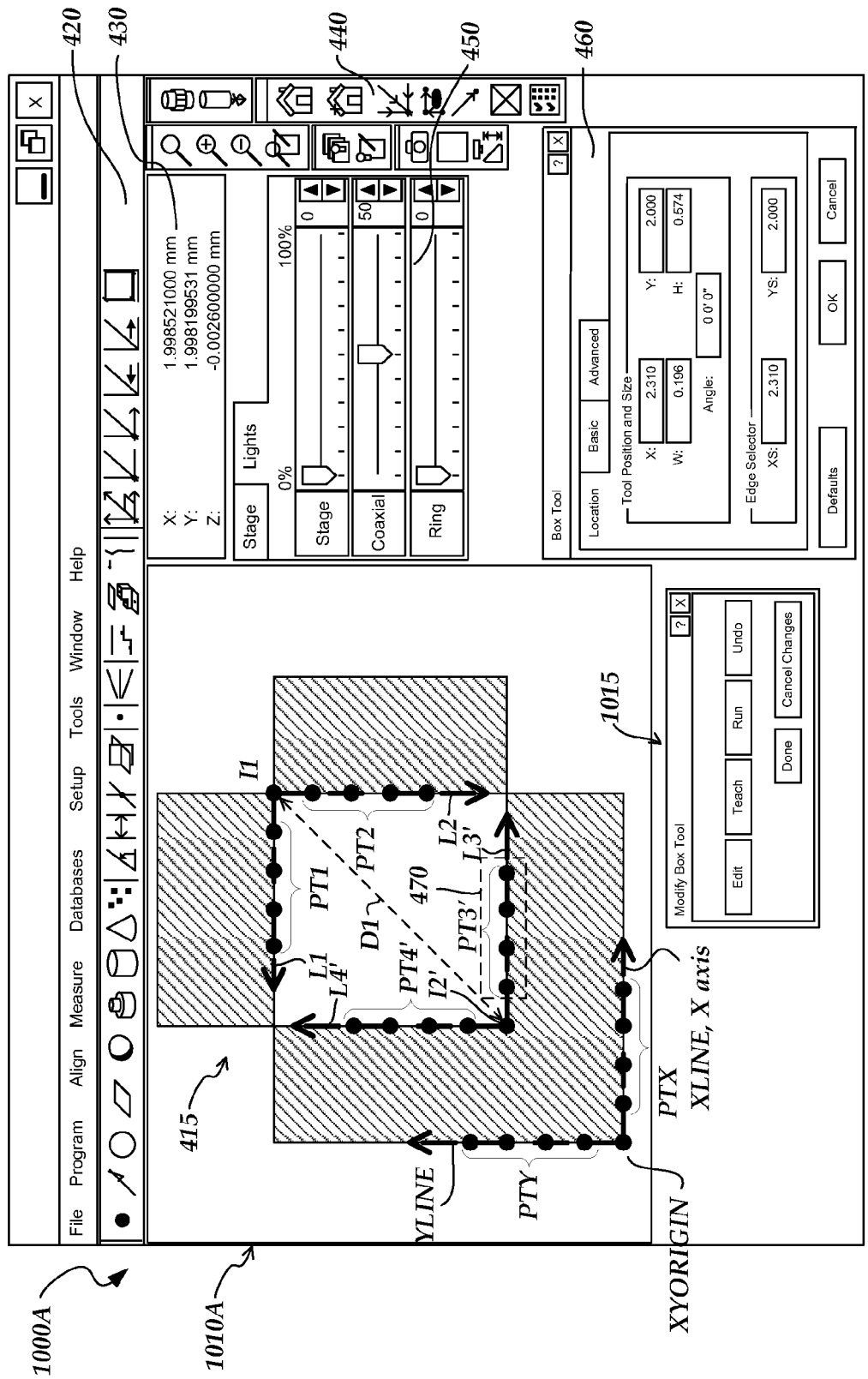
FIGS. 10A and 10B are diagrams of the user interface of FIG. 8 in which a "box tool" video tool has been modified by editing.
Figure 10B:
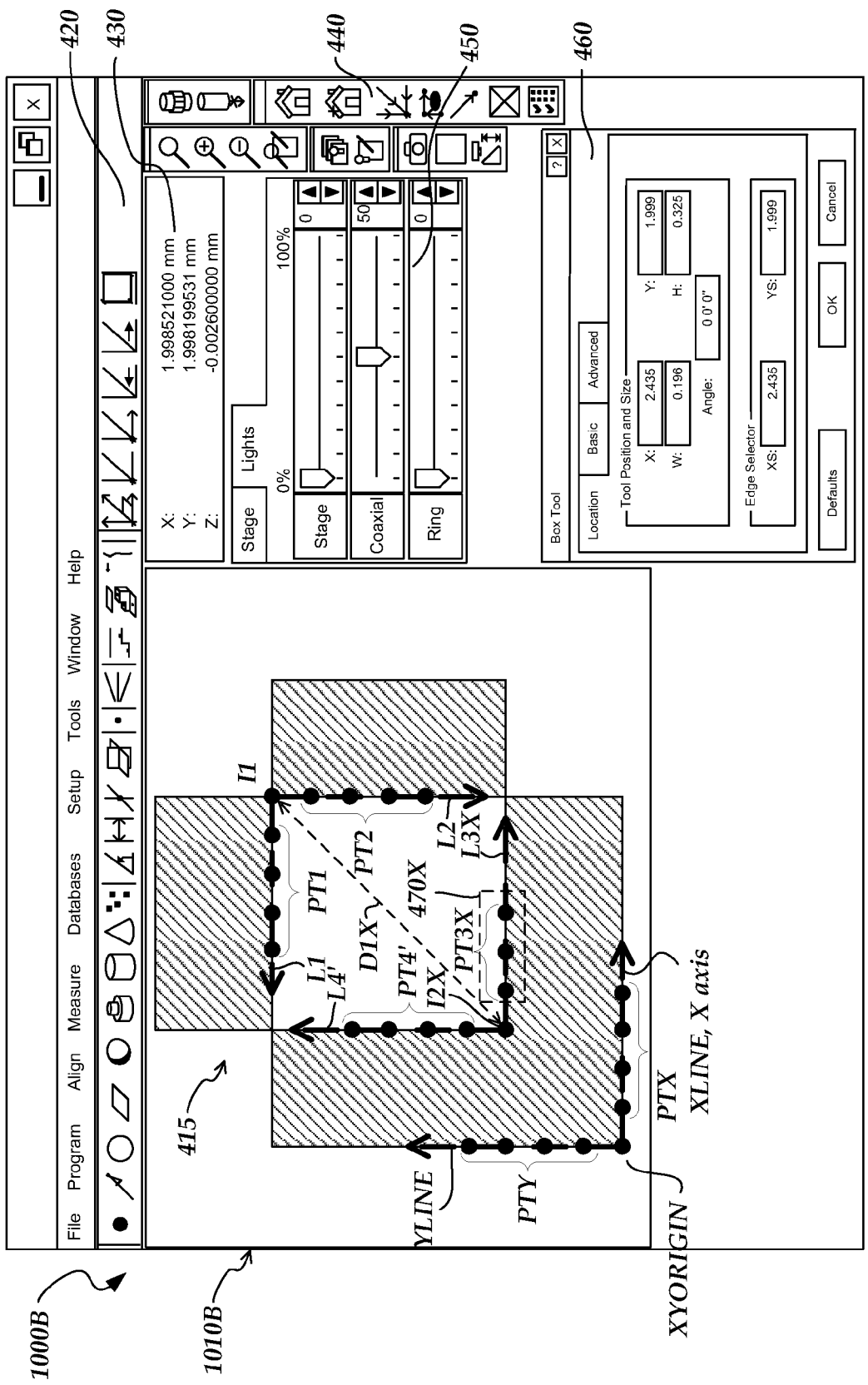

FIGS. 10A and 10B are diagrams of user interfaces 1000A and 1000B which illustrate a modification in the size of the box tool corresponding to the instruction representation 361B of FIG. 9. The user interface 1000A of FIG. 10A illustrates the saved configuration of the box tool 470 corresponding to the instruction representation 361B (i.e., as designated in the XML-like code of FIGS. 5A and 5B and as shown in FIG. 4). In addition, a query box 1015 is provided for the "modify box tool" operations. As shown in the user interface 1000B of FIG. 10B, the user has made modifications which result in a modified box tool 470X. The modified box tool 470X is of a different size and correspondingly determines a different set of edge points PT3X which result in a different determination of a line L3X, as well as an intersection point I2X and a distance D1X. Due to the length (i.e., the height) of the box tool being made shorter, the set of determined edge points PT3X is smaller than the set of previously determined edge points PT3. More specifically, the set of edge points PT3X is shown to include three edge points, while the previously determined set of edge points PT3 had included four edge points. The reduced length (i.e., height) of the box tool is also indicated in the height indicator of the area 460 of the user interface 1000B, which shows a height of 0.32536, as compared to the height of 0.57428 indicated in the area 460 of the user interface 400 of FIG. 4. The modifications resulting in the smaller set of edge points PT3X also produce changes in the corresponding surrogate data, as will be described in more detail below with respect to FIGS. 11A and 11B.

FIGS. 11A and 11B are diagrams 1100A and 1100B of mark-up language code instructions which include surrogate data that has been altered according to the modification of the part program that is illustrated in FIGS. 10A and 10B. It will be appreciated that the XML-like code instructions of FIGS. 11A and 11B are similar to those of FIGS. 5A and 5B. As shown in FIG. 11A, the reduction in the length (i.e., height) is illustrated as part of the data 1120, for which the height is shown to have been reduced to 0.32536 (i.e., as compared to the height of 0.57428 as shown in FIG. 5A). As shown in FIG. 11B, the data 1130 includes only three detected edge points (i.e., as compared to the four detected edge points shown in the saved data 530 of FIG. 5B). It will also be appreciated that the locations of the three detected edge points in the data 1130 is slightly different than the locations of the first three detected edge points in the data 530. In certain implementations, this results from the fact that during actual run mode execution, when a part program is rerun, the measurement data that is returned may be slightly different from different executions.

Figure 12A:
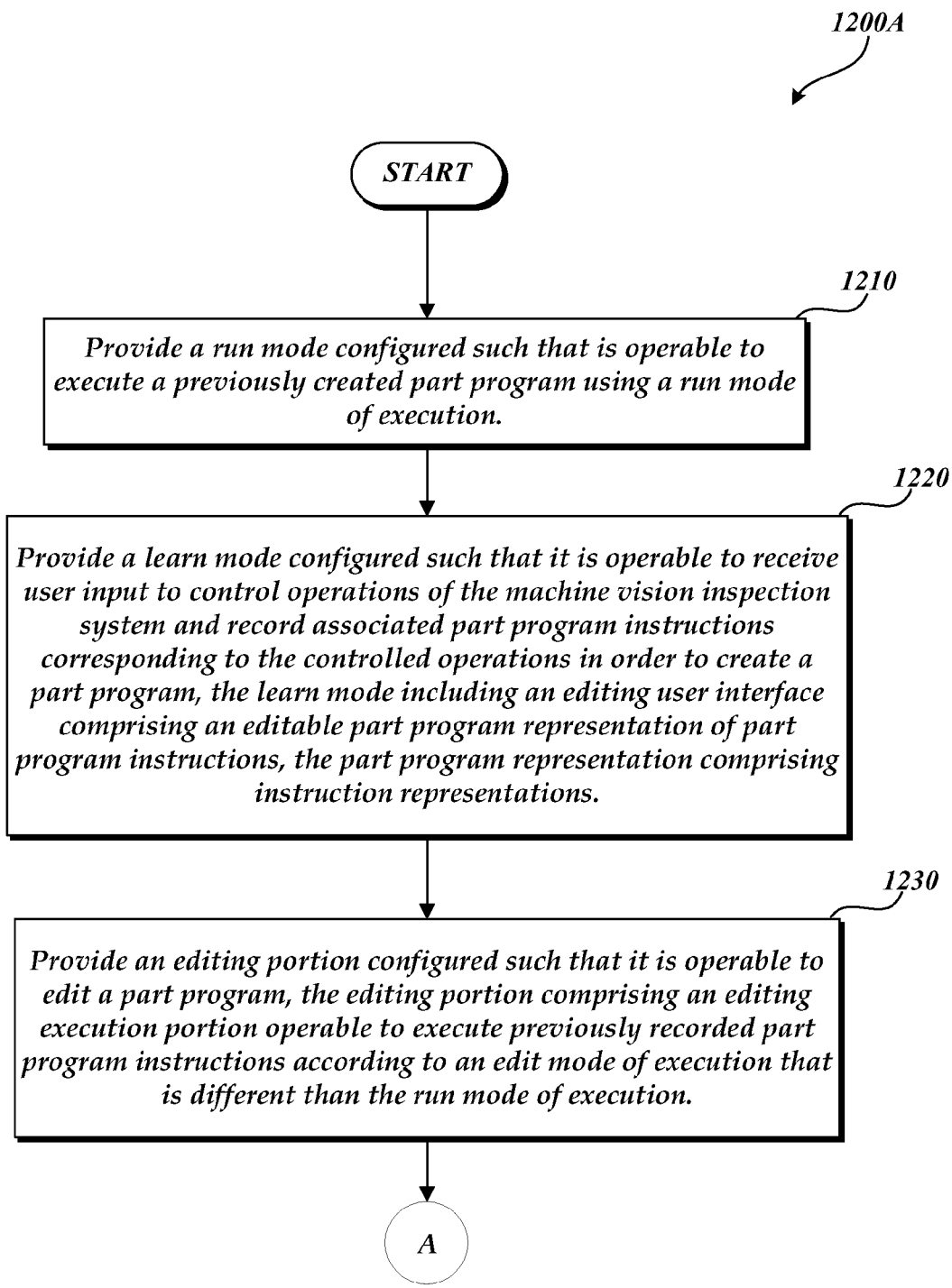
FIGS. 12A and 12B are flow diagrams illustrating one embodiment of a routine for providing a machine vision system program editing environment that includes real time context generation features.
Figure 12B:
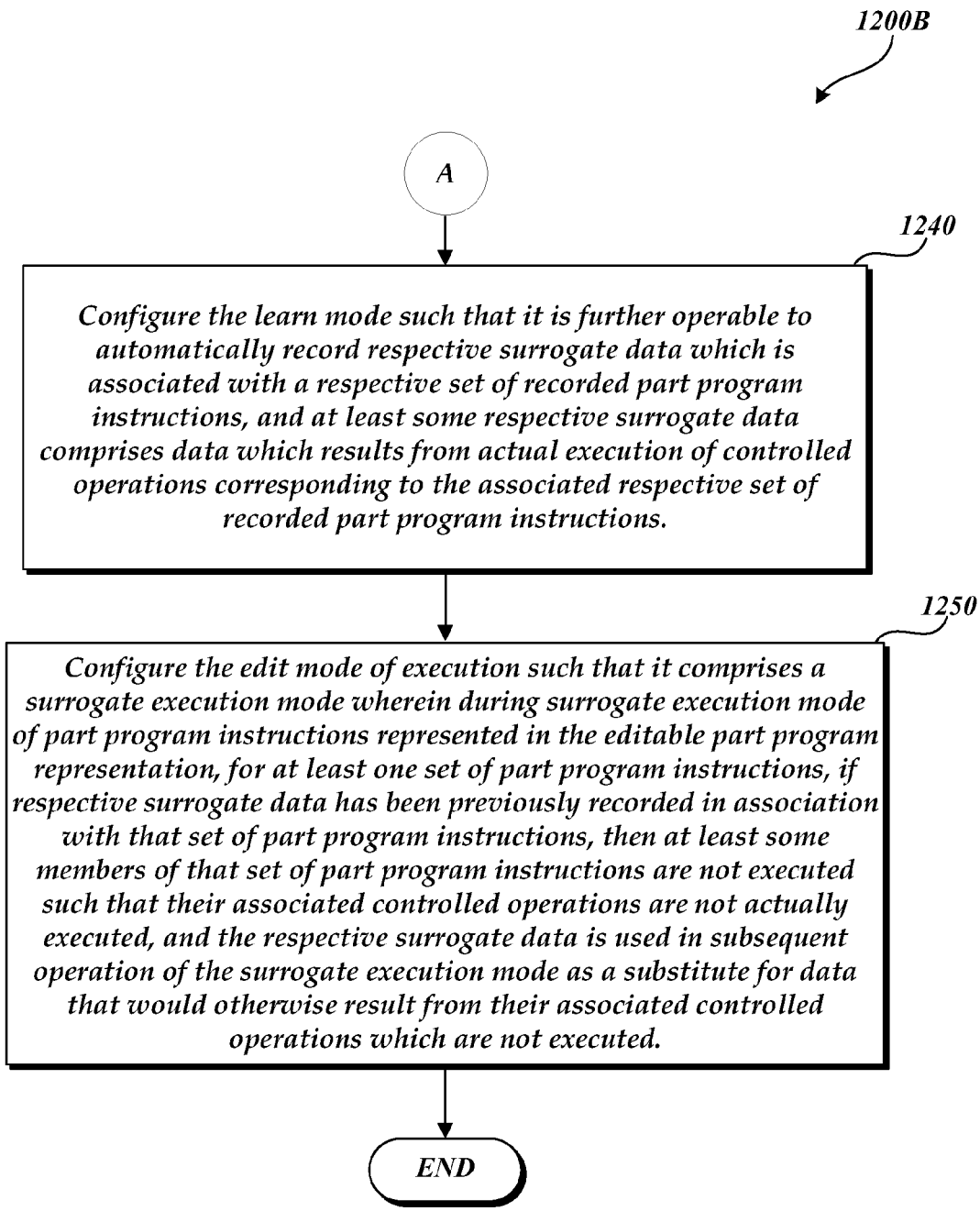

FIGS. 12A and 12B are flow diagrams illustrating one embodiment of a routine 1200 for providing a machine vision system program editing environment that includes real time context generation features. As shown in FIG. 12A, at a block 1210, a run mode is provided that is configured such that it is operable to execute a previously-created part program using a run mode of execution. At a block 1220, a learn mode is provided that is configured such that it is operable to receive user input to control operations of the machine vision inspection system and record associated part program instructions corresponding to the controlled operations in order to create a part program. In addition, the learn mode is made to include an editing user interface comprising an editable part program representation of part program instructions, the part program representation comprising instruction representations. At a block 1230, an editing portion is provided that is configured such that it is operable to edit a part program. In addition, the editing portion comprises an editing execution portion operable to execute previously recorded part program instructions according to an edit mode of execution that is different than the run mode of execution. From the block 1230, the routine continues to a point A, as will be described in more detail below with respect to FIG. 12B.

As shown in FIG. 12B, from the point A, the routine continues to a block 1240. At the block 1240, the learn mode is configured such that it is further operable to automatically record respective surrogate data which is associated with a respective set of recorded part program instructions. In addition, at least some respective surrogate data comprises data which results from actual execution of controlled operations corresponding to the associated respective set of recorded part program instructions. At a block 1250, the edit mode of execution is configured such that it comprises a surrogate execution mode wherein during surrogate execution mode of part program instructions represented in the editable part program representation, for at least one set of part program instructions, if respective surrogate data has been previously recorded in association with that set of part program instructions, then at least some members of that set of part program instructions are not executed such that their associated controlled operations are not actually executed. In addition, the respective surrogate data is used in subsequent operation of the surrogate execution mode as a substitute for data that would otherwise result from their associated controlled operations which are not executed.

Figure 13:
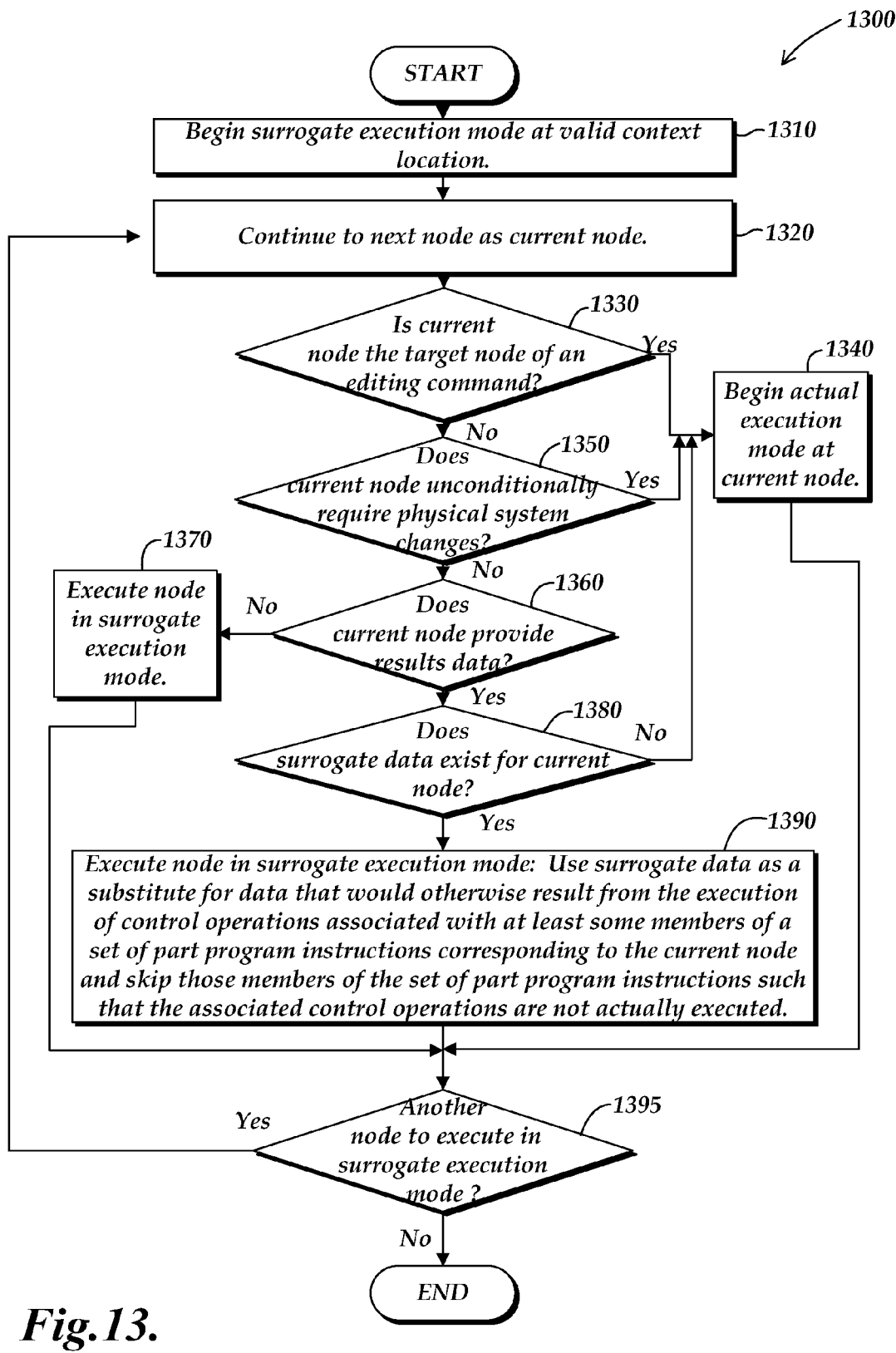
FIG. 13 is a flow diagram illustrating one embodiment of a routine for performing a surrogate execution mode in order to provide a valid editing context at a part program location indicated by part program instruction representation, element, or node.

FIG. 13 is a flow diagram illustrating one embodiment of a routine 1300 for performing a surrogate execution mode in order to provide a valid editing context at a part program location indicated by part program instruction representation, element, or node. At a block 1310, the surrogate execution mode is begun at a valid context location. As a specific example of a valid context location, in the embodiment of FIGS. 7 and 8, a valid context location would be at the instruction representation 361, immediately after the editing initialization block 650 had been run. In other words, due to the editing initialization block 650 having just been executed, the context it generates is known to be valid, such that the surrogate execution mode may begin immediately following it. In an alternative embodiment where no editing initialization block 650 is included, a valid context location may, in one example implementation, exist primarily at the beginning of the part program.

At a block 1320, the routine continues to the next node as a current node. At a decision block 1330, a determination is made as to whether the current node is the target node of an editing command. If the current node is the target node of an editing command, then the routine continues to a block 1340, where an actual execution mode is begun at the current node, after which the routine continues to a decision block 1395, as will be described in more detail below. As a specific example of a current node being the target node of an editing command, in the embodiment of FIGS. 9-11B, the instruction representation 361B is the one that has been selected for editing with the modify command 622. However, because the instruction representation 361B is designated as child node of the parent node for the instruction representation 361, the actual execution mode may be begun at the parent node corresponding to the instruction representation 361. Thus, in one implementation, the target node may be considered to be the parent node associated with the instruction representation 361, and the actual execution mode may start at the parent node such that the physical set up for measurement corresponding to instruction representation 361A is performed to provide the correct physical context for editing at the instruction representation 361B.

If, at the decision block 1330, it is determined that the current node is not the target node of an editing command, then the routine continues to a decision block 1350, where a determination is made as to whether the current node unconditionally requires physical system changes. For example, if the node moves the stage to image a new portion of the workpiece (e.g., via a simple "move" command, or the like), then in some embodiments this may unconditionally require physical system changes. Similarly, certain magnification changes are unconditional physical system changes, and so on. However, it will be appreciated that in some embodiments, if such changes are embedded within a parent node that already has associated surrogate data, and a subsequent node again requires a similar physical change (e.g., a move or magnification change, respectively), then it may not be unconditionally required, since it will eventually be superseded by the similar subsequent instruction. Various methods of analyzing whether a current node unconditionally requires physical system changes may be determined by one skilled in the art, based on the teachings of this disclosure. In any case, if the current node does unconditionally require physical system changes, then the routine continues to the block 1340. If the current node does not unconditionally require physical system changes, then the routine continues to a decision block 1360.

At the decision block 1360, a determination is made as to whether the current node provides results data. If the current node does provide results data, then the routine continues to a decision block 1380, as will be described in more detail below. If the current node does not provide results data, then the routine continues to a block 1370, where the node is executed in surrogate execution mode, after which the routine continues to the block 1395, as will be described in more detail below.

At the decision block 1380, a determination is made as to whether surrogate data exists for the current node. If surrogate data does exist for the current node, then the routine continues to a block 1390, as will be described in more detail below. If surrogate data does not exist for the current node, then the routine continues to the block 1340.

At the block 1390, the node is executed in surrogate execution mode. For the surrogate execution mode, surrogate data is used as a substitute for data that would otherwise result from the execution of control operations associated with at least some members of a set of part program instructions corresponding to the current node, and those members of the set of part program instructions are skipped such that the associated control operations are not actually executed. As a specific example, in the embodiment of FIGS. 7 and 8, the surrogate data (e.g., data 530 of FIG. 5B) is utilized as a substitute for the data that would otherwise result from the execution of the control operations associated with the instruction representations 361, 361A, and 361B, such that the associated instructions and control operations are skipped and not actually executed. Similarly, surrogate data is also used with regard to the operations associated with the instruction representations 362 and 362A, such that the associated instructions and control operations are skipped and not actually executed. In contrast, the instructions associated with the instruction representations 361C (i.e., for defining the line L3' utilizing the surrogate data edge points), the instruction representation 362B (i.e., for defining the line L4' utilizing the surrogate data edge points), and the instruction representation 364 (i.e., for determining the intersection point I2' between the lines L3' and L4') are all executed to generate the associated context. In other words, the generation of the lines L3' and L4' and the intersection point I2', as illustrated in the user interface 800 of FIG. 8, demonstrates how surrogate data may be utilized to generate context for continuing edits to the part program.

The routine then continues to the decision block 1395, where a determination is made as to whether there is another node to execute in the surrogate execution mode. If there is another node to execute in the surrogate execution mode, then the routine returns to the block 1320, and if not, then the routine ends. For example, if execution has arrived at decision block 1395 by reaching a target node and executing blocks 1330 and 1340, then in some instances there will not be another node to execute in surrogate execution mode because the context may already be established for editing at, or within, the target node.

While various preferred and exemplary embodiments of the invention have been illustrated and described, it will be appreciated that various changes can be made therein without departing from the spirit and scope of the invention.

The embodiments of the invention in which an exclusive property or privilege is claimed are defined as follows:

1. A machine vision inspection system comprising an imaging portion, a stage for holding one or more workpieces in a field of view (FOV) of the imaging portion, a control portion including a processor, a display, and a user interface, wherein the machine vision inspection system further comprises:
   a run mode configured such that it is operable to execute a previously-created part program using a run mode of execution;
   a learn mode configured such that it is operable to receive user input to control operations of the machine vision inspection system and record associated part program instructions corresponding to the controlled operations in order to create a part program, the learn mode including an editing user interface comprising an editable part program representation of part program instructions, the part program representation comprising instruction representations; and
   an editing portion configured such that it is operable to edit a part program, the editing portion comprising an editing execution portion operable to execute previously recorded part program instructions according to an edit mode of execution that is different than the run mode of execution,
   wherein:
   the learn mode is configured such that it is further operable to automatically record respective surrogate data which is associated with a respective set of recorded part program instructions, and at least some respective surrogate data comprises data which results from actual execution of controlled operations corresponding to the associated respective set of recorded part program instructions; and the edit mode of execution comprises a surrogate execution mode wherein during surrogate execution mode of part program instructions represented in the editable part program representation, for at least one set of part program instructions, if respective surrogate data has been previously recorded in association with that set of part program instructions, then at least some members of that set of part program instructions are not executed, such that their associated controlled operations are not actually executed, and the respective surrogate data is used in subsequent operation of the surrogate execution mode as a substitute for data that would otherwise result from their associated controlled operations which are not executed.

2. The machine vision inspection system of claim 1, wherein creating a part program comprises modifying a previously recorded part program instruction.

3. The machine vision inspection system of claim 1, wherein the at least some respective surrogate data comprises data which results from actual execution of controlled operations that are controlled based on received user input, and those controlled operations are recorded to provide the associated respective set of recorded part program instructions.

4. The machine vision inspection system of claim 1, wherein the edit mode of execution comprises an actual execution mode, and the at least some respective surrogate data comprises data which results from actual execution of controlled operations that are controlled based on executing a previously recorded associated respective set of recorded part program instructions using the actual execution mode.

5. The machine vision inspection system of claim 1, wherein the machine vision inspection system comprises a program status managing portion that is operable to save the recorded part program instructions in an editable part program file, and when the recorded part program instructions are saved as an editable part program file, respective surrogate data which is associated with a respective set of recorded part program instructions in the editable part program file are also saved.

6. The machine vision inspection system of claim 5, wherein the machine vision inspection system is operable to load the saved editable part program file for editing, and the machine vision inspection system is configured such that when the saved editable part program file is loaded for editing, the associated saved respective surrogate data are automatically made available for use in the surrogate execution mode.

7. The machine vision inspection system of claim 5, wherein the program status managing portion is further operable to save the recorded part program instructions in a protected part program file that is executable using the run mode of execution, wherein at least one of the run mode of execution and the protected part program file is configured such that the results of the run mode of execution are not affected by any previously recorded surrogate data corresponding to the protected part program file.

8. The machine vision inspection system of claim 7, wherein:
the learn mode is configured to record in a respective set of recorded part program instructions an indication of whether respective surrogate data has been previously recorded in association with that respective set of part program instructions; and
the program status managing portion is configured to remove indications of whether respective surrogate data has been previously recorded in association with a respective set of part program instructions, prior to saving the recorded part program instructions in the protected part program file.

9. The machine vision inspection system of claim 1, wherein the learn mode is configured to record in a respective set of recorded part program instructions an indication of whether respective surrogate data has been previously recorded in association with that respective set of part program instructions.

10. The machine vision inspection system of claim 9, wherein the indication is included in an initial instruction of the respective set of recorded part program instructions.

11. The machine vision inspection system of claim 10, wherein the respective set of recorded part program instructions comprise instructions written in a mark-up language.

12. The machine vision inspection system of claim 10, wherein the respective set of recorded part program instructions comprise at least one of an element, a parent element, a container element, and a child element written in a mark-up language.

13. The machine vision inspection system of claim 12, wherein the wherein when the respective set of recorded part program instructions is a parent element, then any child element within that parent element is not executed.

14. The machine vision inspection system of claim 9, wherein the indication comprises the presence of respective surrogate data included within that respective set of recorded part program instructions.

15. The machine vision inspection system of claim 9 wherein the indication comprises a respective identifier included within that respective set of recorded part program instructions, the respective identifier usable to locate the corresponding respective surrogate data in a surrogate data memory portion of the machine vision inspection system.

16. The machine vision inspection system of claim 1, wherein the editing portion comprises editing commands usable to edit a part program, and the editing execution portion is configured such that when the user uses the editing user interface to input an editing command to edit the program at a target location indicated in the part program representation, then the edit mode of execution begins at a valid context starting location in the part program prior to the target location, and uses the surrogate execution mode for executing at least a portion of the part program instructions, in order to establish a valid context for editing the part program at the target location.

17. The machine vision inspection system of claim 16, wherein the input editing command is a command for modifying a part program at the target location, and the part program instruction located at the target location is a previously recorded part program instruction that is to be modified.

18. The machine vision inspection system of claim 16, wherein the input editing command is a command for inserting or appending instructions into the part program at the target location, and the part program instruction located at the target location is a part program instruction that is to be created and inserted or appended at the target location.

19. The machine vision inspection system of claim 16, wherein establishing the valid context at the target location includes establishing the hardware state of the machine vision inspection system in an expected or proper state for executing control operations corresponding to a part program instruction located at the target location.

20. The machine vision inspection system of claim 19, wherein the valid context starting location in the part program comprises one of (a) the beginning of the part program instructions and (b) the next instruction after an editing initialization block comprising part program instructions.

21. The machine vision inspection system of claim 16, wherein the learn mode is configured such that when the valid context is established at the target location, the learn mode user interface is configured to display learn mode user interface elements that are operable by a user to edit and insert part program instructions at the target location, those learn mode user interface elements comprising video tool selection elements.

22. The machine vision inspection system of claim 16, wherein the learn mode is configured such that when the valid context is established at the target location, the learn mode user interface is configured to display a context status indicator proximate to the indication of the target location indicated in the part program representation, and the context status indicator is set to indicate that a valid context has been established at the target location.

23. The machine vision inspection system of claim 22, wherein the learn mode is configured such that when the edit mode of execution uses the surrogate execution mode for executing at least a portion of the part program instructions in order to establish the valid context, then the state of the context status indicator is set to a state that specifically indicates that the surrogate execution mode has been used to establish the valid context.

24. The machine vision inspection system of claim 23, wherein the context status indicator is on instruction pointer included proximate to the editable part program representation.

25. The machine vision inspection system of claim 23, wherein the edit mode of execution comprises an actual execution mode which provides actual execution of controlled operations that are controlled based on executing a previously recorded set of part program instructions, and the editing user interface includes a control operable by the user to use the actual execution mode for executing a set of part program instructions that are sufficient to establish a valid context for editing the part program at a target location.

26. The machine vision inspection system of claim 25, wherein the learn mode is configured such that when the edit mode of execution uses exclusively the actual execution mode for executing the part program instructions that are sufficient to establish the valid context, then the context status indicator is set to a state that specifically indicates that the actual execution mode has been used to establish the valid context.

27. The machine vision inspection system of claim 26, wherein the learn mode is configured such that when a valid context has not been established at the target location, then the state of the context status indicator is set to indicate that the context is at least one of unknown or not valid.

28. The machine vision inspection system of claim 16, wherein the edit mode of execution by default automatically begins at the valid context starting location.

29. The machine vision inspection system of claim 16, wherein the edit mode of execution by default automatically uses the surrogate execution mode for executing at least a portion of the part program instructions.

30. The machine vision inspection system of claim 16, wherein the edit mode of execution comprises an actual execution mode which provides actual execution of controlled operations that are controlled based on executing a previously recorded set of part program instructions, and when the target location is represented within a target parent element represented in the editable part program representation, then the surrogate execution mode comprises switching to the actual execution mode at a starting location of part program instructions corresponding to the target parent element.

31. The machine vision inspection system of claim 30, wherein the target location comprises an instruction that controls an operation corresponding to a video tool that analyzes an acquired image, and the target parent element comprises an instruction that controls an operation of the machine vision inspection system in order to set up the image acquisition conditions for the acquired image.

32. The machine vision inspection system of claim 16, wherein the edit mode of execution comprises an actual execution mode which provides actual execution of controlled operations that are controlled based on executing a previously recorded set of part program instructions, and the surrogate execution mode comprises switching to the actual execution mode of the part program instructions for instructions that unconditionally require physical system changes in order to establish the valid context.

33. The machine vision inspection system of claim 16, wherein the edit mode of execution comprises an actual execution mode which provides actual execution of controlled operations that are controlled based on executing a previously recorded set of part program instructions, and the surrogate execution mode comprises switching to the actual execution mode for a set of the part program instructions which provide results data during run mode execution and for which the corresponding surrogate data is not currently recorded for use as a substitute for the results data that would otherwise result from their associated controlled operations.

34. The machine vision inspection system of claim 16, wherein the edit mode of execution comprises an actual execution mode which provides actual execution of controlled operations that are controlled based on executing a previously recorded set of part program instructions, and the surrogate execution mode comprises switching to the actual execution mode for at least some part program instructions that control operations that change the physical location of the stage relative to the imaging portion, and the learn mode user interface comprises a query box that asks if the user approves of actual execution mode operations comprising moving the physical location stage prior to the actual execution of that move.

35. The machine vision inspection system of claim 1, wherein the edit mode of execution is configured such that, when at least one of the previously recorded part program instructions is modified to provide a modified part program instruction using editing commands, and the modified part program instruction is accepted for recording in the part program, the associated control operations are actually executed and the associated surrogate data is generated and saved.

36. The machine vision inspection system of claim 35, wherein the surrogate data is derived from analysis of workpiece images of an actual workpiece positioned on the stage, wherein the images are acquired during a period corresponding to the modification and recording of the modified part program instruction.

37. The machine vision inspection system of claim 1, wherein the set of part program instructions includes instructions that perform image acquisition operations and an edge detection video tool comprising edge detection operations that identify the edge point positions of points located along a detected edge in that acquired image, if executed, and the surrogate data comprises edge point positions.

38. The machine vision inspection system of claim 37, wherein during the surrogate execution mode at least the image acquisition operations and the edge detection operations are not executed.

39. The machine vision inspection system of claim 1, wherein the machine vision inspection system is a software emulator of an actual machine vision inspection system that emulates the controlled hardware of that actual machine vision inspection system such that it supports virtual operation by part program instructions usable on the actual machine vision inspection system, and by controlled operations input by the user through the user interface of the machine vision inspection system.

40. The machine vision inspection system of claim 39, wherein the workpiece comprises workpiece data configured to provide a virtual workpiece that operates in conjunction with the software emulator of the actual machine vision inspection system.

41. The machine vision inspection system of claim 1, wherein the learn mode comprises a learn mode user interface including a results window that displays results due to the execution of part program instructions, and the learn mode is configured such that when the particular results are surrogate data results based on using the surrogate execution mode for execution of part program instructions, then the learn mode user interface is configured to display a results status indicator proximate to the surrogate data results, and the results status indicator is set to indicate that those particular results are based on surrogate data.

* * * * *